United States Patent [19]
Gold et al.

[11] Patent Number: 5,811,533
[45] Date of Patent: *Sep. 22, 1998

[54] HIGH-AFFINITY OLIGONUCLEOTIDE LIGANDS TO VASCULAR ENDOTHELIAL GROWTH FACTOR (VEGF)

[75] Inventors: Larry Gold; Nebojsa Janjic, both of Boulder, Colo.

[73] Assignee: NeXstar Pharmaceuticals, Inc., Boulder, Colo.

[*] Notice: The term of this patent shall not extend beyond the expiration date of Pat. No. 5,459,015.

[21] Appl. No.: 447,169

[22] Filed: May 19, 1995

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and a continuation-in-part of Ser. No. 964,624, Oct. 21, 1992, Pat. No. 5,496,938, and a continuation-in-part of Ser. No. 205,515, Mar. 3, 1994, abandoned, and a continuation-in-part of Ser. No. 233,012, Apr. 25, 1994.

[51] Int. Cl.$^6$ .......................... C07H 21/02; C07H 21/04; C12P 19/34; C12Q 1/68
[52] U.S. Cl. .......................... 536/23.1; 536/25.4; 435/6; 435/91.2; 935/77; 935/78
[58] Field of Search ................. 536/23.1, 25.4; 435/6, 91.2, 77, 78

[56] References Cited

U.S. PATENT DOCUMENTS

| | | | |
|---|---|---|---|
| 5,270,163 | 12/1993 | Gold et al. | 435/6 |
| 5,459,015 | 10/1995 | Janjic et al. | 435/6 |
| 5,476,766 | 12/1995 | Gold et al. | 435/6 |

FOREIGN PATENT DOCUMENTS

| | | |
|---|---|---|
| 2 183 661 | 6/1987 | United Kingdom . |
| WO 89/06694 | 7/1989 | WIPO . |
| WO 92/14843 | 9/1992 | WIPO . |

OTHER PUBLICATIONS

Breier et al. (1992) Development 114:521.
De Vries et al. (1992) Science 255:989.
Dvorak (1991) J. Exp. Med. 174:1275.
Ferrara et al. (1991) J. Cell. Biochem. 47:211.
Ferrara et al. (1992) Endocrine Rev. 13:18.
Folkman and Klagsbrun (1987) Science 235:442.
Galland et al. (1993) Oncogene 8:1233.
Gill and von Hippel (1989) Anal. Biochem. 182:319.
Gitay–Goren (1992) J. Biol. Chem. 267:6093.
Gutell et al. (1992) Nucl. Acid. Res. 20:5785.
Jakeman et al. (1992) J. Clin. Invest. 89:244.
James et al. (1988) Meth. Enzymol. 180:227.
Kim et al. (1993) Nature 362:841.
Lowary et al. (1987) Nucl. Acids Res. 15:10483.
Milligan et al. (1987) Nucl. Acids Res. 15:8783.
Myoken et al. (1991) Proc. Natl. Acad. Sci. USA 88:5819.
Pepper et al. (1992) Biochem. Biophys. Res. Commun. 189:824.
Peretz et al. (1992) Biochem. Biophys. Res. Commun. 182:1340.
Plate et al. (1992) Nature 359:845.
Schneider et al. (1992) J. Mol. Biol. 228:862.
Senger et al. (1983) Science 219:983.
Shweiki et al. (1992) Nature 359:843.
Tuerk et al. (1990) J. Mol. Biol. 213:749.
Tuerk and Gold (1990) Science 249:505.
Unemori et al. (1993) J. Cell. Physiology 153:557.
Vaisman et al. (1990) J. Biol. Chem. 265:19461.
Yarus and Berg (1970) Anal. Biochem. 35:450.
Yeo et al. (1991) Biochem. Biophys. Res. Commun. 179:1568.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

Methods are described for the identification and preparation of nucleic acid ligands to vascular endothelial growth factor (VEGF). Included in the invention are specific RNA ligands to VEGF identified by the SELEX method.

18 Claims, 13 Drawing Sheets

Starting RNA:
5'-GGGAGCUCAGAAUAAACGCUCAA[-30N-]UUCGACAUGAGGCCCGGAUCCGGC-3'
(SEQ ID NO: 1)

PCR Primer 1:
         Hind III
         ------
5'-CCGAAGCTTAATACGACTCACTATAGGGAGCTCAGAATAAACGCTCAA-3'
              T7 Promoter
              -----------
(SEQ ID NO: 2)

PCR Primer 2:
         Bam H1
         ------
5'-GCCGGATCCGGGCCTCATGTCGAA-3'
(SEQ ID NO: 3)

FAMILY 1

```
                                                                          SEQ ID NO:
  1                            ucaaGAGUGAUGCU-CAUCCGCACUUGGUGACGUU         4
  3  (9)                       caaUACCGGCAUGCAUGUC-CAUCGCUAGCGGGUAuucg      5
  5                             aaUGCGUGUUGACGCA-CAUCCGCACGGCAuu            6
  7  (4)                       ucaaGGAGUGAUGCCCUAUCCGCACCUUGGCCCA            7
  9                              ucaaGCUUGACNGCCCAUCCGAGCUUGAUCACGC          8
 46                         aaacgcucaaUCCUUGAUGCG-GAUCCGAGGAUGGGACGUUu      9
 50                         ACACCGUCGACCUAGUCGC-CAUCCGCACucgac             10
100                          aaCCGGUAGUCGCAUGGCCCAUCCGCCGGuucgac            11
107                         acgcucaaGUCAGCAUGGCCCACCGGCUUGACGUCUG          12
112                        CACGGUUCGAUCUGUACGUU-CAUCCGCACuucga             13
119                      aacgcucaaGGAGCAGUGACGCA-CAUCCACACUCCAGCGuu        14
```

```
|....|....|....|....|....|....|....|....|
1    5   10   15   20   25   30   35   40
```

FAMILY 2

| | | SEQ ID NO: |
|---|---|---|
| 24 (3) | UUCGAAUGCCGAGGCUC--GUGCCUUGACGGGuuc | 15 |
| 34 | UCGCGAAUGCCGACCACU---CAGGUUGAUGGGuucg | 16 |
| 102 | ucaaUGCCGGCUGA---UCGGCUGAUGGGUUGACCG | 17 |
| 128 | GAAUGCCGAGCCCUAAGAGGCUUGAUGUGGuu | 18 |

```
           5'-aaCCUUNAUGUGGCNCGAAC
27              UGCGUGCCGAGGuu-3'                    19

5'-aaGCUUGAUGGGUGACACAC
44              GUCAUGCCGAGCuu-3'                    20

5'-GUCGUCCCUGCAUGGGCCGUAU
55              CGGUGCGCG-3'                         21
```

|....|....|....|....|....|....|....|....|
1    5   10   15   20   25   30   35   40

FIGURE 2B

```
FAMILY 3                                                              SEQ ID NO:

12 (7)       GCAGAGCGAAGGG-AACCUGCGUCUCGGCACCuucg                          22
 28           AAGGAGG-ANCCUGCGUCUCGGCACUCCGCA                               23
 75 (1)       ucaaGGG-AACCUGCGUUCGGCACCUUGUUCCGU                            24
137           aaAUGUGGGUUACCUGCGUUCGGCACCACGUuu                             25

|....|....|....|....|....|....|....|....|
       1    5   10   15   20   25   30   35   40

FIGURE 2C

FAMILY 4                                                              SEQ ID NO:

6                          CGACGGUAGAGUCUGUCCCGUCAUCCCCCA                 26
 35                AAAGACCCCUGGUUGAGUCUGUCCCAGCCGuu                         27
 40           GACCCAUCGUCAACGGUUGAGUCUGUCCCGUucgacaugagg                    28
 56                 gcucaaGGUUGAGUCUGUCCUUGGAGUAUCUGAUC                     29
 90                   UCGGACAGUUGGUUGAGUCUGUCCAACUUuu                       30
106                  GACCAUGUGACUGGUUGAGCCUGUCCCAGuu                        31
138                      AACGGUUGAGUCUGUCCGUAAGAGAGCGC                      32

|....|....|....|....|....|....|....|....|
       1    5   10   15   20   25   30   35   40

FIGURE 2D
```

FAMILY 5

| | | SEQ ID NO: |
|---|---|---|
| 15 | UCGGAAUGUAGUUGACGUAUCCUUGU--CCGAuucgacau | 33 |
| 20 | aGGGUAGUUGGGACCUA--GUCCGCCGUACCuu | 34 |
| 21 | GGCAUAGUUGGGACCUC--GUCCGCCGUGCCC | 35 |
| 84 | gcucaaUAGUUGGAGGCCUGCCUCGCCGUAGAGCG | 36 |

FAMILY 6

| | | SEQ ID NO: |
|---|---|---|
| 25 | aGGGGUUCUA-GUGGAGACUCUGCCGGCCCuu | 37 |
| 126(2) | aACGGUUCUGUGUGGACUA-GCCGGGGCCGuu | 38 |

Family 3 (SEQ ID NO: 44)

Family 2 (SEQ ID NO: 43)

Family 1 (SEQ ID NO: 42)

Family 6
(SEQ ID NO: 47)

Family 5
(SEQ ID NO: 46)

Family 4
(SEQ ID NO: 45)

5,811,533

SEQUENCE LISTING ( 1 ) GENERAL INFORMATION:

( i i i ) NUMBER OF SEQUENCES: 242

( 2 ) INFORMATION FOR SEQ ID NO:1:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGGAGCUCAG  AAUAAACGCU  CAANNNNNN   NNNNNNNNN   NNNNNNNNN    5 0

NNNUUCGACA  UGAGGCCCGG  AUCCGGC                               7 7
```

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CCGAAGCTTA  ATACGACTCA  CTATAGGGAG  CTCAGAATAA  ACGCTCAA     4 8
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GCCGGATCCG  GGCCTCATGT  CGAA                                  2 4
```

( 2 ) INFORMATION FOR SEQ ID NO:4:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GGGAGCUCAG  AAUAAACGCU  CAAGAGUGAU  GCUCAUCCGC  ACUUGGUGAC    5 0
```

GUUUUCGACA UGAGGCCCGG AUCCGGC    77

( 2 ) INFORMATION FOR SEQ ID NO:5:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGGAGCUCAG AAUAAACGCU CAAUACCGGC AUGCAUGUCC AUCGCUAGCG    50

GUAUUCGACA UGAGGCCCGG AUCCGGC    77

( 2 ) INFORMATION FOR SEQ ID NO:6:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGGAGCUCAG AAUAAACGCU CAAUGCGUGU UGUGACGCAC AUCCGCACGC    50

GCAUUCGACA UGAGGCCCGG AUCCGGC    77

( 2 ) INFORMATION FOR SEQ ID NO:7:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGGAGCUCAG AAUAAACGCU CAAGGAGUGA UGCCCUAUCC GCACCUUGGC    50

CCAUUCGACA UGAGGCCCGG AUCCGGC    77

( 2 ) INFORMATION FOR SEQ ID NO:8:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GGGAGCUCAG AAUAAACGCU CAAGCUUGAC NGCCCAUCCG AGCUUGAUCA    50

CGCUUCGACA UGAGGCCCGG AUCCGGC    77

( 2 ) INFORMATION FOR SEQ ID NO:9:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GGGAGCUCAG AAUAAACGCU CAAUCCUUGA UGCGGAUCCG AGGAUGGGAC    50

GUUUCGACA UGAGGCCCGG AUCCGGC    77

( 2 ) INFORMATION FOR SEQ ID NO:10:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( x i ) SEQUENCE DESCRIPTION: SEQ ID NO:10:

```
GGGAGCUCAG  AAUAAACGCU  CAAACACCGU  CGACCUAUGA  UGCGCAUCCG      50

CACUUCGACA  UGAGGCCCGG  AUCCGGC                                 77
```

( 2 ) INFORMATION FOR SEQ ID NO:11:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( x i ) SEQUENCE DESCRIPTION: SEQ ID NO:11:

```
GGGAGCUCAG  AAUAAACGCU  CAACCGGUAG  UCGCAUGGCC  CAUCGCGCCC      50

GGUUCGACAU  GAGGCCCGGA  UCCGGC                                  76
```

( 2 ) INFORMATION FOR SEQ ID NO:12:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( x i ) SEQUENCE DESCRIPTION: SEQ ID NO:12:

```
GGGAGCUCAG  AAUAAACGCU  CAAGUCAGCA  UGGCCCACCG  CGCUUGACGU      50

CUGUUCGACA  UGAGGCCCGG  AUCCGGC                                 77
```

( 2 ) INFORMATION FOR SEQ ID NO:13:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( x i ) SEQUENCE DESCRIPTION: SEQ ID NO:13:

```
GGGAGCUCAG  AAUAAACGCU  CAACACGGUU  CGAUCUGUGA  CGUUCAUCCG      50

CACUUCGACA  UGAGGCCCGG  AUCCGGC                                 77
```

( 2 ) INFORMATION FOR SEQ ID NO:14:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( x i ) SEQUENCE DESCRIPTION: SEQ ID NO:14:

```
GGGAGCUCAG  AAUAAACGCU  CAAGGAGCAG  UGACGCACAU  CCACACUCCA      50

GCGUUCGACA  UGAGGCCCGG  AUCCGGC                                 77
```

( 2 ) INFORMATION FOR SEQ ID NO:15:

( i ) SEQUENCE CHARACTERISTICS:
( A ) LENGTH: 77 base pairs
( B ) TYPE: nucleic acid
( C ) STRANDEDNESS: single 5,811,533

27

-continued ( D ) TOPOLOGY: linear ( x i ) SEQUENCE DESCRIPTION: SEQ ID NO:15:

GGGAGCUCAG AAUAAACGCU CAAUUCGAAU GCCGAGGCUC GUGCCUUGAC       50

GGGUUCGACA UGAGGCCCGG AUCCGGC                                77

( 2 ) INFORMATION FOR SEQ ID NO:16:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGGAGCUCAG AAUAAACGCU CAAUCGCGAA UGCCGACCAC UCAGGUUGAU       50

GGGUUCGACA UGAGGCCCGG AUCCGGC                                77

( 2 ) INFORMATION FOR SEQ ID NO:17:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGAGCUCAG AAUAAACGCU CAAUGCCGGC CUGAUCGGCU GAUGGGUUGA       50

CCGUUCGACA UGAGGCCCGG AUCCGGC                                77

( 2 ) INFORMATION FOR SEQ ID NO:18:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGGAGCUCAG AAUAAACGCU CAAGAAUGCC GAGCCCUAAG AGGCUUGAUG       50

UGGUUCGACA UGAGGCCCGG AUCCGGC                                77

( 2 ) INFORMATION FOR SEQ ID NO:19:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGGAGCUCAG AAUAAACGCU CAACCUUNAU GUGGCNCGAA CUGCGUGCCG       50

AGGUUCGACA UGAGGCCCGG AUCCGGC                                77

( 2 ) INFORMATION FOR SEQ ID NO:20:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGGAGCUCAG AAUAAACGCU CAAGCUUGAU GGGUGACACA CGUCAUGCCG       50

AGCUUCGACA UGAGGCCCGG AUCCGGC 77

( 2 ) INFORMATION FOR SEQ ID NO:21:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GGGAGCUCAG AAUAAACGCU CAAGUCGUCC UGCAUGGGCC GUAUCGGUGC 50

GCGUUCGACA UGAGGCCCGG AUCCGGC 77

( 2 ) INFORMATION FOR SEQ ID NO:22:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GGGAGCUCAG AAUAAACGCU CAAGCAGACG AAGGGAACCU GCGUCUCGGC 50

ACCUUCGACA UGAGGCCCGG AUCCGGC 77

( 2 ) INFORMATION FOR SEQ ID NO:23:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GGGAGCUCAG AAUAAACGCU CAAAAGGAGG ANCCUGCGUC UCGGCACUCC 50

GCAUUCGACA UGAGGCCCGG AUCCGGC 77

( 2 ) INFORMATION FOR SEQ ID NO:24:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GGGAGCUCAG AAUAAACGCU CAAGGGAACC UGCGUUUCGG CACCUUGUUC 50

CGUUUCGACA UGAGGCCCGG AUCCGGC 77

( 2 ) INFORMATION FOR SEQ ID NO:25:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GGGAGCUCAG AAUAAACGCU CAAAAAUGUG GGUUACCUGC GUUUCGGCAC 50

CACGUUUCGA CAUGAGGCCC GGAUCCGGC 79

( 2 ) INFORMATION FOR SEQ ID NO:26:

( i ) SEQUENCE CHARACTERISTICS:
  ( A ) LENGTH: 77 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:26:

```
GGGAGCUCAG  AAUAAACGCU  CAACGACGGU  AGAGUCUGUC  CCGUCAUCCC    50
CCAUUCGACA  UGAGGCCCGG  AUCCGGC                                77
```

( 2 ) INFORMATION FOR SEQ ID NO:27:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

```
GGGAGCUCAG  AAUAAACGCU  CAAAAAGACC  CCUGGUUGAG  UCUGUCCCAG    50
CCGUUCGACA  UGAGGCCCGG  AUCCGGC                                77
```

( 2 ) INFORMATION FOR SEQ ID NO:28:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

```
GGGAGCUCAG  AAUAAACGCU  CAAGACCCAU  CGUCAACGGU  UGAGUCUGUC    50
CCGUUCGACA  UGAGGCCCGG  AUCCGGC                                77
```

( 2 ) INFORMATION FOR SEQ ID NO:29:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

```
GGGAGCUCAG  AAUAAACGCU  CAAGGUUGAG  UCUGUCCCUU  CGAGUAUCUG    50
AUCUUCGACA  UGAGGCCCGG  AUCCGGC                                77
```

( 2 ) INFORMATION FOR SEQ ID NO:30:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

```
GGGAGCUCAG  AAUAAACGCU  CAAUCGGACA  GUUGGUUGAG  UCUGUCCCAA    50
CUUUUCGACA  UGAGGCCCGG  AUCCGGC                                77
```

( 2 ) INFORMATION FOR SEQ ID NO:31:

( i ) SEQUENCE CHARACTERISTICS:
    ( A ) LENGTH: 76 base pairs
    ( B ) TYPE: nucleic acid
    ( C ) STRANDEDNESS: single ( D ) TOPOLOGY: linear ( x i ) SEQUENCE DESCRIPTION: SEQ ID NO:31:

| GGGAGCUCAG | AAUAAACGCU | CAAGACCAUG | UGACUGGUUG | AGCCUGUCCC | 50 |
| AGUUCGACAU | GAGGCCCGGA | UCCGGC | | | 76 |

( 2 ) INFORMATION FOR SEQ ID NO:32:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

| GGGAGCUCAG | AAUAAACGCU | CAAAACGGUU | GAGUCUGUCC | CGUAAGAGAG | 50 |
| CGCUUCGACA | UGAGGCCCGG | AUCCGGC | | | 77 |

( 2 ) INFORMATION FOR SEQ ID NO:33:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

| GGGAGCUCAG | AAUAAACGCU | CAAUCGGAAU | GUAGUUGACG | UAUCCUUGUC | 50 |
| CGAUUCGACA | UGAGGCCCGG | AUCCGGC | | | 77 |

( 2 ) INFORMATION FOR SEQ ID NO:34:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

| GGGAGCUCAG | AAUAAACGCU | CAAGGGUGUA | GUUGGGACCU | AGUCCGCCGU | 50 |
| ACCUUCGACA | UGAGGCCCGG | AUCCGGC | | | 77 |

( 2 ) INFORMATION FOR SEQ ID NO:35:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

| GGGAGCUCAG | AAUAAACGCU | CAAGGCAUAG | UUGGGACCUC | GUCCGCCGUG | 50 |
| CCCUUCGACA | UGAGGCCCGG | AUCCGGC | | | 77 |

( 2 ) INFORMATION FOR SEQ ID NO:36:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

| GGGAGCUCAG | AAUAAACGCU | CAAUAGUUGG | AGGCCUGUCC | UCGCCGUAGA | 50 |

GCGUUCGACA UGAGGCCCGG AUCCGGC 77

( 2 ) INFORMATION FOR SEQ ID NO:37:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GGGAGCUCAG AAUAAACGCU CAAGGGGUUC UAGUGGAGAC UCUGCCGCGG 50

CCCUUCGACA UGAGGCCCGG AUCCGGC 77

( 2 ) INFORMATION FOR SEQ ID NO:38:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

GGGAGCUCAG AAUAAACGCU CAAACGGUUC UGUGUGUGGA CUAGCCGCGG 50

CCGUUCGACA UGAGGCCCGG AUCCGGC 77

( 2 ) INFORMATION FOR SEQ ID NO:39:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GGGAGCUCAG AAUAAACGCU CAAGGGAUGU UUGGCUAUCU CGGAUAGUGC 50

CCCUUCGACA UGAGGCCCGG AUCCGGC 77

( 2 ) INFORMATION FOR SEQ ID NO:40:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGGAGCUCAG AAUAAACGCU CAAGCUUAAU ACGACUCACU NUAGGGAGCU 50

CAGUUCGACA UGAGGCCCGG AUCCGGC 77

( 2 ) INFORMATION FOR SEQ ID NO:41:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GGGAGCUCAG AAUAAACGCU CAAUUGAGUG AUGUGCUUGA CGUAUCGCUG 50

CACUUCGACA UGAGGCCCGG AUCCGGC 77

( 2 ) INFORMATION FOR SEQ ID NO:42:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ii) MOLECULE TYPE: RNA (ix) FEATURE:
  (A) NAME/KEY: N
  (B) LOCATION: 15
  (C) OTHER INFORMATION: This symbol stands
      for the complimentary base for the N
      located in position 1

(xi) SEQUENCE DESCRIPTION: SEQ ID NO:42:

NUGAUGVNCA UCCGN                                                                   15

(2) INFORMATION FOR SEQ ID NO:43:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: RNA (ix) FEATURE:
    (A) NAME/KEY: S
    (B) LOCATION: 11 and 12
    (C) OTHER INFORMATION: This symbol stands
        for the complimentary base for the S
        located in positions 9 and 10

(xi) SEQUENCE DESCRIPTION: SEQ ID NO:43:

AAUGCCGASS SSUUGAUGGG UU                                                           22

(2) INFORMATION FOR SEQ ID NO:44:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: RNA (ix) FEATURE:
    (A) NAME/KEY: H
    (B) LOCATION: 24
    (C) OTHER INFORMATION: This symbol stands
        for the complimentary base for the D
        located in position 2

(ix) FEATURE:
    (A) NAME/KEY: Y
    (B) LOCATION: 25
    (C) OTHER INFORMATION: This symbol stands
        for the complimentary base for the R
        located in position 25

(ii) MOLECULE TYPE: RNA (xi) SEQUENCE DESCRIPTION: SEQ ID NO:44:

RDGGGAACCU GCGU YUCGGC ACCH Y                                                      25

(2) INFORMATION FOR SEQ ID NO:45:

(i) SEQUENCE CHARACTERISTICS:
    (A) LENGTH: 19 base pairs
    (B) TYPE: nucleic acid
    (C) STRANDEDNESS: single ( D ) TOPOLOGY: linear ( i i ) MOLECULE TYPE: RNA ( i x ) FEATURE:
    ( A ) NAME/KEY: D
    ( B ) LOCATION: 18 and 19
    ( C ) OTHER INFORMATION: This symbol stands
        for the complimentary base for the H
        located in positions 1 and 2

( x i ) SEQUENCE DESCRIPTION: SEQ ID NO:45:

HHGGUUGAGU CUGUCCCDD 19

( 2 ) INFORMATION FOR SEQ ID NO:46:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: N
        ( B ) LOCATION: 18-20 and 27
        ( C ) OTHER INFORMATION: This symbol stands
            for the complimentary base for the N
            located in positions 1 and 10-12

( x i ) SEQUENCE DESCRIPTION: SEQ ID NO:46:

NRUAGUUGGN NNCUNSUNNN CGCCGUN 27

( 2 ) INFORMATION FOR SEQ ID NO:47:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: M
        ( B ) LOCATION: 20
        ( C ) OTHER INFORMATION: This symbol stands
            for the complimentary base for the K
            located in position 14

( i x ) FEATURE:
        ( A ) NAME/KEY: S
        ( B ) LOCATION: 31
        ( C ) OTHER INFORMATION: This symbol stands
            for the complimentary base for the S
            located in position 2

( x i ) SEQUENCE DESCRIPTION: SEQ ID NO:47:

RSGGUUUCRU GUGKRGACUM UGCCGCGGCC SU 32

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGGAACCUGC GU Y UCGGCAC C 21

( 2 ) INFORMATION FOR SEQ ID NO:49:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

GGUUGAGUCU GUCCC     15

( 2 ) INFORMATION FOR SEQ ID NO:50:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AAGCAGACGA AGGGAACCUG CGUCUCGGCA CCUUCGACAU     40

( 2 ) INFORMATION FOR SEQ ID NO:51:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GGCCGGUAGU CGCAUGGCCC AUCGCGCCCG G     31

( 2 ) INFORMATION FOR SEQ ID NO:52:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GGAAGCUUGA UGGGUGACAC ACGUCAUGCC GAGCU     35

( 2 ) INFORMATION FOR SEQ ID NO:53:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

GGAAGGGAAC CUGCGUCUCG GCACCUUCG     29

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GGUCAACGGU UGAGUCUGUC CCGUUCGAC     29

( 2 ) INFORMATION FOR SEQ ID NO:55:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:55:

GGCUCAAUAG UUGGAGGCCU GUCCUCGCCG UAGAGC        36

( 2 ) INFORMATION FOR SEQ ID NO:56:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:56:

GGAACGGUUC UGUGUGUGGA CUAGCCGCGG CCGUU          35

( 2 ) INFORMATION FOR SEQ ID NO:57:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:57:

GGGAGACAAG AAUAACGCUC AANNNNNNNN NNNNNNNNN NNNNNNNNN     50

NNUUCGACAG GAGGCUCACA ACAGGC                             76

( 2 ) INFORMATION FOR SEQ ID NO:58:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:58:

TAATACGACT CACTATAGGG AGACAAGAAU AACGCUCAA     39

( 2 ) INFORMATION FOR SEQ ID NO:59:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:59:

| GCCTGTTGTG AGCCTCCTGT CGAA | 2 4 |

( 2 ) INFORMATION FOR SEQ ID NO:60:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:60:

| GGGAGGACGA UGCGGNNNNN NNNNNNNNN NNNNNNNNN NNNNNNNNN | 5 0 |
| NNNNNNNNN NNNNCAGAC GACTCGCCCG A | 8 1 |

( 2 ) INFORMATION FOR SEQ ID NO:61:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:61:

| TAATACGACT CACTATAGGG AGGACGAUGC GG | 3 2 |

( 2 ) INFORMATION FOR SEQ ID NO:62:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:62:

| TCGGGCGAGT CGTCTG | 1 6 |

( 2 ) INFORMATION FOR SEQ ID NO:63:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:63:

| GGGAGGACGA UGCGGUGGCU GUGAUCAAUG CGGGGAGGUG AGGAAGGGCC | 5 0 |

UUACAAAUCC UUCGGCAGAC GACTCGCCCG A            81

( 2 ) INFORMATION FOR SEQ ID NO:64:

( i ) SEQUENCE CHARACTERISTICS:
  ( A ) LENGTH: 81 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-NH$_2$ cytosine ( i x ) FEATURE:
  ( D ) OTHER INFORMATION: All U'S are 2'-NH$_2$ uracil ( x i ) SEQUENCE DESCRIPTION: SEQ ID NO:64:

GGGAGGACGA UGCGGUGUGA UCAAUGCGGU GGCGGGGUAU GGAUGGGAGU            50

CUGGAAUGCU GCGCUCAGAC GACTCGCCCG A            81

( 2 ) INFORMATION FOR SEQ ID NO:65:

( i ) SEQUENCE CHARACTERISTICS:
  ( A ) LENGTH: 80 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-NH$_2$ cytosine ( i x ) FEATURE:
  ( D ) OTHER INFORMATION: All U'S are 2'-NH$_2$ uracil ( x i ) SEQUENCE DESCRIPTION: SEQ ID NO:65:

GGGAGGACGA UGCGGCGCUG UGUUCAAUGC GGGGAUCGGG CCGGAGGAUG            50

AACAAAUGGC GGGUCAGACG ACTCGCCCGA            80

( 2 ) INFORMATION FOR SEQ ID NO:66:

( i ) SEQUENCE CHARACTERISTICS:
  ( A ) LENGTH: 81 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-NH$_2$ cytosine ( i x ) FEATURE:
  ( D ) OTHER INFORMATION: All U'S are 2'-NH$_2$ uracil ( x i ) SEQUENCE DESCRIPTION: SEQ ID NO:66:

GGGAGGACGA UGCGGUGUUG AGCAAGCACU CAUGGGUCA AUGUGGGAGU            50

GGGAGCUGGU GGGGUCAGAC GACTCGCCCG A            81

( 2 ) INFORMATION FOR SEQ ID NO:67:

( i ) SEQUENCE CHARACTERISTICS:
  ( A ) LENGTH: 81 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-NH$_2$ cytosine ( i x ) FEATURE:
  ( D ) OTHER INFORMATION: All U'S are 2'-NH$_2$ uracil ( x i ) SEQUENCE DESCRIPTION: SEQ ID NO:67:

GGGAGGACGA UGCGGCAAGG GAGCGUUAGA GCCAUGUGGU CAAUGAGGGG 50

UGGGAUUGGU UGGGUCAGAC GACTCGCCCG A 81

( 2 ) INFORMATION FOR SEQ ID NO:68:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:68:

GGGAGGACGA UGCGGCAUGG UUGUGAACUG UUGUGAUCAA UGCGGGGAGG 50

GUAAUGGUGG GUGGUCAGAC GACTCGCCCG A 81

( 2 ) INFORMATION FOR SEQ ID NO:69:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:69:

GGGAGGACGA UGCGGAUGAG UGACACAUGU GCUCAAUGCG GGGUGGGUUG 50

GUAGGGGUAG CACGGCAGAC GACTCGCCCG A 81

( 2 ) INFORMATION FOR SEQ ID NO:70:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:70:

GGGAGGACGA UGCGGUGUGG UCAAUGUGGG GUAGGGCUGG UAGGGCAUUC 50

CGUACUGGUG UGGUCAGACG ACTCGCCCGA 80

( 2 ) INFORMATION FOR SEQ ID NO:71:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-NH$_2$ uracil ( x i ) SEQUENCE DESCRIPTION: SEQ ID NO:71:

| | | | | | |
|---|---|---|---|---|---|
| GGGAGGACGA | UGCGGCCGAG | UUGUGCUCAA | UGUGGGGUCU | GGGUACGGAC | 50 |
| GGGAACAGAU | CUGGCAGACG | ACTCGCCCGA | | | 80 |

( 2 ) INFORMATION FOR SEQ ID NO:72:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:72:

| | | | | | |
|---|---|---|---|---|---|
| GGGAGGACGA | UGCGGGUGCU | CAGCAUUGUG | UGCUCAAUGC | GGGGGAGUUU | 50 |
| GGGUUGGCGA | CGGCAGACGA | CTCGCCCGA | | | 79 |

( 2 ) INFORMATION FOR SEQ ID NO:73:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:73:

| | | |
|---|---|---|
| UGUGNUCAAU | GNGGGG | 16 |

( 2 ) INFORMATION FOR SEQ ID NO:74:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:74:

| | | | | | |
|---|---|---|---|---|---|
| GGGAGGACGA | UGCGGCAUAG | GCUUACAACA | GAGCGGGGU | UCUGAUGGUA | 50 |
| GACGCCGGGA | CGCCCCAGAC | GACTCGCCCG | A | | 81 |

( 2 ) INFORMATION FOR SEQ ID NO:75:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
  ( D ) OTHER INFORMATION: All C'S are 2'-NH$_2$ cytosine ( i x ) FEATURE:
  ( D ) OTHER INFORMATION: All U'S are 2'-NH$_2$ uracil ( x i ) SEQUENCE DESCRIPTION: SEQ ID NO:75:

GGGAGGACGA UGCGGUAUGA UGGUAGACGC CGUACCGCAU CAGGCCAAGU    50

CGUCACAGAU CGUGCAGACG ACTCGCCCGA    80

( 2 ) INFORMATION FOR SEQ ID NO:76:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:76:

GGGAGACAAG AAUAACGCUC AAGCAACAGA GGCUGAUGGU AGACGCCGGC    50

CAUUCGACAG GAGGCUCACA ACAGGC    76

( 2 ) INFORMATION FOR SEQ ID NO:77:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:77:

GGGAGACAAG AAUAACGCUC AAAGAGUCGC UGAUGGUAGA CGCCGGCGGA    50

UCUUCGACAG GAGGCUCACA ACAGGC    76

( 2 ) INFORMATION FOR SEQ ID NO:78:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:78:

GGGAGACAAG AAUAACGCUC AAGAGGCUGA UGGCAGACGC GGCCGAAGAC    50

AUUCGACAGG AGGCUCACAA CAGGC    75

( 2 ) INFORMATION FOR SEQ ID NO:79:

( i ) SEQUENCE CHARACTERISTICS:
    ( A ) LENGTH: 75 base pairs ( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:79:

GGGAGACAAG AAUAACGCUC AACCCUGAUG GUAGACGCCG GGGUGCCGGA 50

AUUCGACAGG AGGCUCACAA CAGGC 75

( 2 ) INFORMATION FOR SEQ ID NO:80:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:80:

CUGAUGGUAG ACGCCGG 17

( 2 ) INFORMATION FOR SEQ ID NO:81:

( i ) SEQUENCE CHARACTERISTICS:
( A ) LENGTH: 82 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:81:

GGGAGGACGA UGCGGCAGUG CUGAACUAAU CGAACGGGGU CAAGGAGGGU 50

CGAACGAGAU CUGCCGCAGA CGACTCGCCC GA 82

( 2 ) INFORMATION FOR SEQ ID NO:82:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:82:

GGGAGGACGA UGCGGCACCU UCGUGGGGUC AAGGAGGGUC GCGAGGCCGC 50

AGGAUCAACC GUGUGCAGAC GACTCGCCCG A 81

( 2 ) INFORMATION FOR SEQ ID NO:83:

( i ) SEQUENCE CHARACTERISTICS:
  ( A ) LENGTH: 81 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-NH$_2$ cytosine ( i x ) FEATURE:
  ( D ) OTHER INFORMATION: All U'S are 2'-NH$_2$ uracil ( x i ) SEQUENCE DESCRIPTION: SEQ ID NO:83:

```
GGGAGGACGA UGCGGGGUCA AGUUGGGUCG AGGAAGCGCU CCCGAGUAUC      50

GUAGUGUGCG ACUGCCAGAC GACTCGCCCG A                          81
```

( 2 ) INFORMATION FOR SEQ ID NO:84:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:84:

```
GGGAGACAAG AAUAACGCUC AAGAACUUGA UCGGGGUCAA GGCGGGACGA      50

AUUCGACAGG AGGCUCACAA CAGGC                                 75
```

( 2 ) INFORMATION FOR SEQ ID NO:85:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:85:

```
GGGAGACAAG AAUAACGCUC AAUGGCGGGA CCAAGGAGGG ACGUGUAGGA      50

AAUUCGACAG GAGGCUCACA ACAGGC                                76
```

( 2 ) INFORMATION FOR SEQ ID NO:86:

( i ) SEQUENCE CHARACTERISTICS:
    ( A ) LENGTH: 78 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:86:

```
GGGAGACAAG AAUAACGCUC AAAAAAUGCA CAAAUCGGGG UCAAGGAGGG      50

ACGAUUCGAC AGGAGGCUCA CAACAGGC                              78
```

(2) INFORMATION FOR SEQ ID NO:87:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ix) FEATURE:
        (D) OTHER INFORMATION: All C'S are 2'-$NH_2$ cytosine (ix) FEATURE:
        (D) OTHER INFORMATION: All U'S are 2'-$NH_2$ uracil (xi) SEQUENCE DESCRIPTION: SEQ ID NO:87:

```
GGGAGGACGA  UGCGGAUGGG  UUCGUGUGGU  GAAUGGAGGA  GGUGGGCUCG        50

CAUGCUACUG  UGCAGACGAC  TCGCCCGA                                  78
```

(2) INFORMATION FOR SEQ ID NO:88:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ix) FEATURE:
        (D) OTHER INFORMATION: All C'S are 2'-$NH_2$ cytosine (ix) FEATURE:
        (D) OTHER INFORMATION: All U'S are 2'-$NH_2$ uracil (xi) SEQUENCE DESCRIPTION: SEQ ID NO:88:

```
GGUCAAGGNG  GG                                                    12
```

(2) INFORMATION FOR SEQ ID NO:89:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (D) OTHER INFORMATION: All C'S are 2'-$NH_2$ cytosine (ix) FEATURE:
        (D) OTHER INFORMATION: All U'S are 2'-$NH_2$ uracil (xi) SEQUENCE DESCRIPTION: SEQ ID NO:89:

```
GGGAGGACGA  UGCGGUGCAC  UAAGUCCGGG  UAGUGGGAGU  GGUUGGGCCU        50

GGAGUGCGCC  AGACGACTCG  CCCGA                                     75
```

(2) INFORMATION FOR SEQ ID NO:90:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-$NH_2$ cytosine (ix) FEATURE:
        (D) OTHER INFORMATION: All U'S are 2'-$NH_2$ uracil (xi) SEQUENCE DESCRIPTION: SEQ ID NO:90:

```
GGGAGACAAG  AAUAACGCUC  AAAUCAAAGG  GUAGAGGGUG  GGCUGUGGCA        50
```

AGUUCGACAG GAGGCUCACA ACAGGC 76

( 2 ) INFORMATION FOR SEQ ID NO:91:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:91:

GGGAGACAAG AAUAACGCUC AAAAUCGAGG GUAGCGGGCG CGGCUUGGCC 50

AAUUCGACAG GAGGCUCACA ACAGGC 76

( 2 ) INFORMATION FOR SEQ ID NO:92:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:92:

GGGAGACAAG AAUAACGCUC AAGCCUCGGA UCGGGCAGCG GGUGGGAUGG 50

CAAUUCGACA GGAGGCUCAC AACAGGC 77

( 2 ) INFORMATION FOR SEQ ID NO:93:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:93:

GGGAGACAAG AAUAACGCUC AAAACGGAGU GGUAGGCGUU GGGUGCCAGG 50

AAUUCGACAG GAGGCUCACA ACAGGC 76

( 2 ) INFORMATION FOR SEQ ID NO:94:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:94:

GGUAGNGGGN G                                                                                                            11

( 2 ) INFORMATION FOR SEQ ID NO:95:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:95:

GGGAGGACGA UGCGGAACCG AGUCGUGUGG GUUGGGGCUC CAGUACAUCC              50

CCGGUCUGGG UGUCAGACGA CTCGCCCGA                                     79

( 2 ) INFORMATION FOR SEQ ID NO:96:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:96:

GGGAGGACGA UGCGGUAACA UACGCAGUCG UGUGGGUAGG GGAUCACAAA              50

CUGCGUAUCG UGUCAGACGA CTCGCCCGA                                     79

( 2 ) INFORMATION FOR SEQ ID NO:97:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:97:

GGGAGACAAG AAUAACGCUC AAAGUCGUGU GGGUGGGGUC AUUCGACAGG              50

AGGCUCACAA CAGGC                                                    65

( 2 ) INFORMATION FOR SEQ ID NO:98:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:98:

```
GGGAGACAAG AAUAACGCUC AAAGUGUAGG AUAGGGGAUG GGAGGUCCGG          50
GAUUCGACAG GAGGCUCACA ACAGGC                                   76
```

( 2 ) INFORMATION FOR SEQ ID NO:99:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:99:

```
GGGAGACAAG AAUAACGCUC AAACUGUGGG CUCUAGGGCA GUGGGAGUGG          50
AGUUCGACAG GAGGCUCACA ACAGGC                                   76
```

( 2 ) INFORMATION FOR SEQ ID NO:100:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:100:

```
GGGAGACAAG AAUAACGCUC AAAGUGGGAC AGGGAUUGCG GAGGGUGGAA          50
GGUUCGACAG GAGGCUCACA ACAGGC                                   76
```

( 2 ) INFORMATION FOR SEQ ID NO:101:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:101:

```
GGGAGACAAG AAUAACGCUC AAGUCAGGAG GACUGGAAGG UGGGACUGGU          50
GAUUCGACAG GAGGCUCACA ACAGGC                                   76
```

( 2 ) INFORMATION FOR SEQ ID NO:102:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:102:

```
GGGAGACAAG  AAUAACGCUC  AAGCAGGAGA  GAGGGUGUUG  GGUGCGGAUA       50

CAUUCGACAG  GAGGCUCACA  ACAGGC                                   76
```

( 2 ) INFORMATION FOR SEQ ID NO:103:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:103:

```
GGGAGGACGA  UGCGGAGGGU  AGGAGGCUAA  GCAUAGUUCA  GAGGAGGUGG       50

CGCGUGCCCC  CGUGCAGACG  ACTCGCCCGA                               80
```

( 2 ) INFORMATION FOR SEQ ID NO:104:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:104:

```
GGGAGGACGA  UGCGGCAACA  UUGGCACCAA  UGCUCUGUGU  UAAUGUGGGG       50

UGGGAACGGC  GCCGCAGACG  ACTCGCCCGA                               80
```

( 2 ) INFORMATION FOR SEQ ID NO:105:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:105:

```
GGGAGGACGA  UGCGGACCAA  UGAUUGCAAU  GAGGGCAGUG  GGGGGGAAUU       50

GGGCUCGUGU  GGUCAGACGA  CTCGCCCGA                                79
```

( 2 ) INFORMATION FOR SEQ ID NO:106:

( i ) SEQUENCE CHARACTERISTICS:

( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:106:

| GGGAGGACGA | UGCGGGCAGU | GGGUGAGGUC | CGGGCACGAU | UGAGUUUGAA | 50 |
| CGGUUCUGGC | UUGGUCAGAC | GACTCGCCCG | A | | 81 |

( 2 ) INFORMATION FOR SEQ ID NO:107:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:107:

| GGGAGGACGA | UGCGGGUGGU | AGGUGUAGAG | UGGAUGGCGG | AGGUCCUAGU | 50 |
| AGUUCUGUGC | CUGGUCAGAC | GACTCGCCCG | A | | 81 |

( 2 ) INFORMATION FOR SEQ ID NO:108:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:108:

| GGGAGGACGA | UGCGGCGCGG | GAGAGGGUAG | UGGGUGUGGU | GCUUGGACAA | 50 |
| GCAGCGCAGA | CGACTCGCCC | GA | | | 72 |

( 2 ) INFORMATION FOR SEQ ID NO:109:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:109:

| GGGAGGACGA | UGCGGACCCG | CAUACGGACC | GCGGAGGGGG | AAAUCUAGCC | 50 |
| UCAGGGGUGG | CGGGCCAGAC | GACTCGCCCG | A | | 81 |

( 2 ) INFORMATION FOR SEQ ID NO:110:

( i ) SEQUENCE CHARACTERISTICS:
  ( A ) LENGTH: 80 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-$NH_2$ cytosine ( i x ) FEATURE:
  ( D ) OTHER INFORMATION: All U'S are 2'-$NH_2$ uracil ( x i ) SEQUENCE DESCRIPTION: SEQ ID NO:110:

```
GGGAGGACGA  UGCGGUGAAG  AAGCGGGGAC  UGCACGACGG  GAUGGAGGGA        50

CACGACUGCG  GGGUCAGACG  ACTCGCCCGA                                80
```

( 2 ) INFORMATION FOR SEQ ID NO:111:

( i ) SEQUENCE CHARACTERISTICS:
  ( A ) LENGTH: 76 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-$NH_2$ cytosine ( i x ) FEATURE:
  ( D ) OTHER INFORMATION: All U'S are 2'-$NH_2$ uracil ( x i ) SEQUENCE DESCRIPTION: SEQ ID NO:111:

```
GGGAGACAAG  AAUAACGCUC  AAACACCAGG  AGAGUGGGUU  CGGGUGAGGA        50

CGUUCGACAG  GAGGCUCACA  ACAGGC                                    76
```

( 2 ) INFORMATION FOR SEQ ID NO:112:

( i ) SEQUENCE CHARACTERISTICS:
  ( A ) LENGTH: 76 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-$NH_2$ cytosine ( i x ) FEATURE:
  ( D ) OTHER INFORMATION: All U'S are 2'-$NH_2$ uracil ( x i ) SEQUENCE DESCRIPTION: SEQ ID NO:112:

```
GGGAGACAAG  AAUAACGCUC  AAGUGGCUGA  UGGCAGACGC  CGGCUGCUGA        50

CGUUCGACAG  GAGGCUCACA  ACAGGC                                    76
```

( 2 ) INFORMATION FOR SEQ ID NO:113:

( i ) SEQUENCE CHARACTERISTICS:
  ( A ) LENGTH: 76 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-$NH_2$ cytosine ( i x ) FEATURE:
  ( D ) OTHER INFORMATION: All U'S are 2'-$NH_2$ uracil ( x i ) SEQUENCE DESCRIPTION: SEQ ID NO:113:

GGGAGACAAG AAUAACGCUC AAUCGUGCCA GGACAUGGUG GCUCAUGGGU        50

AAUUCGACAG GAGGCUCACA ACAGGC        76

( 2 ) INFORMATION FOR SEQ ID NO:114:

( i ) SEQUENCE CHARACTERISTICS:
           ( A ) LENGTH: 76 base pairs
           ( B ) TYPE: nucleic acid
           ( C ) STRANDEDNESS: single
           ( D ) TOPOLOGY: linear ( i x ) FEATURE:
           ( D ) OTHER INFORMATION: All C'S are 2'-$NH_2$ cytosine ( i x ) FEATURE:
           ( D ) OTHER INFORMATION: All U'S are 2'-$NH_2$ uracil ( x i ) SEQUENCE DESCRIPTION: SEQ ID NO:114:

GGGAGACAAG AAUAACGCUC AAAGGUACGG GGGAGGGAAG GAUAUAACGC        50

GAUUCGACAG GAGGCUCACA ACAGGC        76

( 2 ) INFORMATION FOR SEQ ID NO:115:

( i ) SEQUENCE CHARACTERISTICS:
           ( A ) LENGTH: 76 base pairs
           ( B ) TYPE: nucleic acid
           ( C ) STRANDEDNESS: single
           ( D ) TOPOLOGY: linear ( i x ) FEATURE:
           ( D ) OTHER INFORMATION: All C'S are 2'-$NH_2$ cytosine ( i x ) FEATURE:
           ( D ) OTHER INFORMATION: All U'S are 2'-$NH_2$ uracil ( x i ) SEQUENCE DESCRIPTION: SEQ ID NO:115:

GGGAGACAAG AAUAACGCUC AAUGGAAAGG UGUGGAAAGA GGCAUCGGGG        50

GGUUCGACAG GAGGCUCACA ACAGGC        76

( 2 ) INFORMATION FOR SEQ ID NO:116:

( i ) SEQUENCE CHARACTERISTICS:
           ( A ) LENGTH: 76 base pairs
           ( B ) TYPE: nucleic acid
           ( C ) STRANDEDNESS: single
           ( D ) TOPOLOGY: linear ( i x ) FEATURE:
           ( D ) OTHER INFORMATION: All C'S are 2'-$NH_2$ cytosine ( i x ) FEATURE:
           ( D ) OTHER INFORMATION: All U'S are 2'-$NH_2$ uracil ( x i ) SEQUENCE DESCRIPTION: SEQ ID NO:116:

GGGAGACAAG AAUAACGCUC AAUCAAUGGG CAGGAAGAGG GAAGGGAUGU        50

GAUUCGACAG GAGGCUCACA ACAGGC        76

( 2 ) INFORMATION FOR SEQ ID NO:117:

( i ) SEQUENCE CHARACTERISTICS:
           ( A ) LENGTH: 76 base pairs
           ( B ) TYPE: nucleic acid
           ( C ) STRANDEDNESS: single
           ( D ) TOPOLOGY: linear ( i x ) FEATURE:
           ( D ) OTHER INFORMATION: All C'S are 2'-$NH_2$ cytosine ( i x ) FEATURE:

(D) OTHER INFORMATION: All U'S are 2'-NH₂ uracil (x i) SEQUENCE DESCRIPTION: SEQ ID NO:117:

GGGAGACAAG AAUAACGCUC AACAUGGGUA AGGGAGUGGG AGUGGUGAAU      50

AGUUCGACAG GAGGCUCACA ACAGGC      76

(2) INFORMATION FOR SEQ ID NO:118:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (i x) FEATURE:
        (D) OTHER INFORMATION: All C'S are 2'-NH₂ cytosine (i x) FEATURE:
        (D) OTHER INFORMATION: All U'S are 2'-NH₂ uracil (x i) SEQUENCE DESCRIPTION: SEQ ID NO:118:

GGGAGACAAG AAUAACGCUC AAGGAACGAG UAGGGCAGUG GGUGGUGAUG      50

GCUUCGACAG GAGGCUCACA ACAGGC      76

(2) INFORMATION FOR SEQ ID NO:119:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (i x) FEATURE:
        (D) OTHER INFORMATION: All C'S are 2'-NH₂ cytosine (i x) FEATURE:
        (D) OTHER INFORMATION: All U'S are 2'-NH₂ uracil (x i) SEQUENCE DESCRIPTION: SEQ ID NO:119:

GGGAGACAAG AAUAACGCUC AAUAGGGCAG AGGGAGUGGU UAGGGCUGUG      50

AUUUCGACAG GAGGCUCACA ACAGGC      76

(2) INFORMATION FOR SEQ ID NO:120:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (i x) FEATURE:
        (D) OTHER INFORMATION: All C'S are 2'-NH₂ cytosine (i x) FEATURE:
        (D) OTHER INFORMATION: All U'S are 2'-NH₂ uracil (x i) SEQUENCE DESCRIPTION: SEQ ID NO:120:

GGGAGACAAG AAUAACGCUC AAGGGUAGUG GGAAGGGUAA GGGCCGAGGU      50

GGUUCGACAG GAGGCUCACA ACAGGC      76

(2) INFORMATION FOR SEQ ID NO:121:

(i) SEQUENCE CHARACTERISTICS:
        (A) LENGTH: 76 base pairs
        (B) TYPE: nucleic acid
        (C) STRANDEDNESS: single
        (D) TOPOLOGY: linear ( i x ) FEATURE:
    ( D ) OTHER INFORMATION: All C'S are 2'-NH$_2$ cytosine ( i x ) FEATURE:
    ( D ) OTHER INFORMATION: All U'S are 2'-NH$_2$ uracil ( x i ) SEQUENCE DESCRIPTION: SEQ ID NO:121:

GGGAGACAAG AAUAACGCUC AAAAUACACA CCGCGGGAAG GGAGGGUGGA        50

AAUUCGACAG GAGGCUCACA ACAGGC        76

( 2 ) INFORMATION FOR SEQ ID NO:122:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:122:

GGGAGACAAG AAUAACGCUC AAAGACUACA GCGCGGGUUA GGGUUGAGGG        50

AAUUCGACAG GAGGCUCACA ACAGGC        76

( 2 ) INFORMATION FOR SEQ ID NO:123:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:123:

GGGAGACAAG AAUAACGCUC AAUACGAGCA AGCGGGCGAA GGGUUGAGGG        50

AAUUCGACAG GAGGCUCACA ACAGGC        76

( 2 ) INFORMATION FOR SEQ ID NO:124:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:124:

GGGAGACAAG AAUAACGCUC AACAAGGUGG UGGAGGAGGA UACGAUCUGC        50

AGUUCGACAG GAGGCUCACA ACAGGC        76

( 2 ) INFORMATION FOR SEQ ID NO:125:

( i ) SEQUENCE CHARACTERISTICS:
        ( A ) LENGTH: 75 base pairs (B) TYPE: nucleic acid
        (C) STRANDEDNESS: single
        (D) TOPOLOGY: linear (ix) FEATURE:
        (D) OTHER INFORMATION: All C'S are 2'-NH$_2$ cytosine (ix) FEATURE:
        (D) OTHER INFORMATION: All U'S are 2'-NH$_2$ uracil (xi) SEQUENCE DESCRIPTION: SEQ ID NO:125:

```
GGGAGACAAG  AAUAACGCUC  AAGGAGGGAA  GGAGGGCAGG  UGAUGGGUCA        50

GUUCGACAGG  AGGCUCACAA  CAGGC                                     75
```

(2) INFORMATION FOR SEQ ID NO:126:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH$_2$ cytosine (ix) FEATURE:
        (D) OTHER INFORMATION: All U'S are 2'-NH$_2$ uracil (xi) SEQUENCE DESCRIPTION: SEQ ID NO:126:

```
GGGAGACAAG  AAUAACGCUC  AAUGAUGGCG  GUAGUGGAGG  UAAUGAGCGU        50

GAUUCGACAG  GAGGCUCACA  ACAGGC                                    76
```

(2) INFORMATION FOR SEQ ID NO:127:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH$_2$ cytosine (ix) FEATURE:
        (D) OTHER INFORMATION: All U'S are 2'-NH$_2$ uracil (xi) SEQUENCE DESCRIPTION: SEQ ID NO:127:

```
GGGAGACAAG  AAUAACGCUC  AAGCAACUGG  GGGCGGGUGG  UGUGAGGAUU        50

CGACAGGAGG  CUCACAACAG  GC                                        72
```

(2) INFORMATION FOR SEQ ID NO:128:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH$_2$ cytosine (ix) FEATURE:
        (D) OTHER INFORMATION: All U'S are 2'-NH$_2$ uracil (xi) SEQUENCE DESCRIPTION: SEQ ID NO:128:

```
GGGAGACAAG  AAUAACGCUC  AAGGAGGGGC  CUAUAGGGGU  GGUGGUGUAC        50

GAUUCGACAG  GAGGCUCACA  ACAGGC                                    76
```

( 2 ) INFORMATION FOR SEQ ID NO:129:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:129:

GGGAGACAAG AAUAACGCUC AAUAUAGGGU AGUGGGUGUA GGUAGGGCGA    50

CAUUCGACAG GAGGCUCACA ACAGGC    76

( 2 ) INFORMATION FOR SEQ ID NO:130:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:130:

GGGAGACAAG AAUAACGCUC AAGAGGGUUG GAGGGCAUGG GGCAGGAACC    50

GGUUCGACAG GAGGCUCACA ACAGGC    76

( 2 ) INFORMATION FOR SEQ ID NO:131:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:131:

GGGAGACAAG AAUAACGCUC AACGUAGAAC UGGCGGGCAG UGGGGGGGAU    50

GCUUCGACAG GAGGCUCACA ACAGGC    76

( 2 ) INFORMATION FOR SEQ ID NO:132:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH$_2$ cytosine ( i x ) FEATURE:
        ( D ) OTHER INFORMATION: All U'S are 2'-NH$_2$ uracil ( x i ) SEQUENCE DESCRIPTION: SEQ ID NO:132:

GGGAGACAAG AAUAACGCUC AAUGAGGGGA CGAGGGAUGU GGGGAGCGGG    50

ACUUCGACAG GAGGCUCACA ACAGGC 76

( 2 ) INFORMATION FOR SEQ ID NO:133:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:133:

GGGAGACAAG AAUAACGCUC AACGAGGGAU GGGAGGCGUG UGGAAGAUGC 50

AAUUCGACAG GAGGCUCACA ACAGGC 76

( 2 ) INFORMATION FOR SEQ ID NO:134:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:134:

GGGAGACAAG AAUAACGCUC AAGCAUCCGG GGACAAGAUG GGUCGGUAAG 50

GUUUCGACAG GAGGCUCACA ACAGGC 76

( 2 ) INFORMATION FOR SEQ ID NO:135:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:135:

GGGAGACAAG AAUAACGCUC AAGUGUGCGG GGUCAAGACG GGUGGCGUGC 50

GUUCGACAGG AGGCUCACAA CAGGC 75

( 2 ) INFORMATION FOR SEQ ID NO:136:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:136:

GGGAGACAAG AAUAACGCUC AAUCAAACCA UGGGGCGGGU GGUACGAGGA  50

ACUUCGACAG GAGGCUCACA ACAGGC  76

( 2 ) INFORMATION FOR SEQ ID NO:137:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:137:

GGGAGACAAG AAUAACGCUC AACGAGUCCG AGGGAUGGGU GGUGUGCGGC  50

AAUUCGACAG GAGGCUCACA ACAGGC  76

( 2 ) INFORMATION FOR SEQ ID NO:138:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:138:

GGGAGACAAG AAUAACGCUC AACAGUGUCG GAGAGGAGGA UGGAGGUAUG  50

AAUUCGACAG GAGGCUCACA ACAGGC  76

( 2 ) INFORMATION FOR SEQ ID NO:139:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-$NH_2$ cytosine ( i x ) FEATURE:
        ( D ) OTHER INFORMATION: All U'S are 2'-$NH_2$ uracil ( x i ) SEQUENCE DESCRIPTION: SEQ ID NO:139:

GGGAGGACGA UGCGGCACCA CUACGCGGGA AGGGUAGGGU GGAUUACAAG  50

GUGUGACCGC UCCGUCAGAC GACTCGCCCG A  81

( 2 ) INFORMATION FOR SEQ ID NO:140:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:

-continued ( D ) OTHER INFORMATION: All C'S are 2'-NH$_2$ cytosine ( i x ) FEATURE:
                ( D ) OTHER INFORMATION: All U'S are 2'-NH$_2$ uracil ( x i ) SEQUENCE DESCRIPTION: SEQ ID NO:140:

GGGAGGACGA    UGCGGUACGG    UUAACGGGGG    UGGUGUGGGA    GGACACAAAG         50

CGCGUACCUG    CCCCCAGACG    ACTCGCCCGA                                     80

( 2 ) INFORMATION FOR SEQ ID NO:141:

( i ) SEQUENCE CHARACTERISTICS:
                ( A ) LENGTH: 81 base pairs
                ( B ) TYPE: nucleic acid
                ( C ) STRANDEDNESS: single
                ( D ) TOPOLOGY: linear ( i x ) FEATURE:
                ( D ) OTHER INFORMATION: All C'S are 2'-NH$_2$ cytosine ( i x ) FEATURE:
                ( D ) OTHER INFORMATION: All U'S are 2'-NH$_2$ uracil ( x i ) SEQUENCE DESCRIPTION: SEQ ID NO:141:

GGGAGGACGA    UGCGGAGGUC    CUCGAGGGUC    UGGGUGUGGG    AGUGGGCAUG         50

GACCAAUACC    GCGUGCAGAC    GACTCGCCCG    A                                81

( 2 ) INFORMATION FOR SEQ ID NO:142:

( i ) SEQUENCE CHARACTERISTICS:
                ( A ) LENGTH: 81 base pairs
                ( B ) TYPE: nucleic acid
                ( C ) STRANDEDNESS: single
                ( D ) TOPOLOGY: linear ( i x ) FEATURE:
                ( D ) OTHER INFORMATION: All C'S are 2'-NH$_2$ cytosine ( i x ) FEATURE:
                ( D ) OTHER INFORMATION: All U'S are 2'-NH$_2$ uracil ( x i ) SEQUENCE DESCRIPTION: SEQ ID NO:142:

GGGAGGACGA    UGCGGAAACC    CAUCCUGCGC    GGGAUGGGAG    GGUGGAAACA         50

CUAGAGCUUC    GCCUGCAGAC    GACTCGCCCG    A                                81

( 2 ) INFORMATION FOR SEQ ID NO:143:

( i ) SEQUENCE CHARACTERISTICS:
                ( A ) LENGTH: 81 base pairs
                ( B ) TYPE: nucleic acid
                ( C ) STRANDEDNESS: single
                ( D ) TOPOLOGY: linear ( i x ) FEATURE:
                ( D ) OTHER INFORMATION: All C'S are 2'-NH$_2$ cytosine ( i x ) FEATURE:
                ( D ) OTHER INFORMATION: All U'S are 2'-NH$_2$ uracil ( x i ) SEQUENCE DESCRIPTION: SEQ ID NO:143:

GGGAGGACGA    UGCGGAACUG    GUGGUCACGC    GUUGAGGUGG    UGGAGGUGGA         50

UUCAACGGUC    GAGGGCAGAC    GACTCGCCCG    A                                81

( 2 ) INFORMATION FOR SEQ ID NO:144:

( i ) SEQUENCE CHARACTERISTICS:
                ( A ) LENGTH: 81 base pairs
                ( B ) TYPE: nucleic acid ( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:144:

GGGAGGACGA UGCGGCAUGA AAGUAGGGUU AUGAAGGCGG UAGAUGGAGG        50

AGGUUGGGUU GCCGCCAGAC GACTCGCCCG A        81

( 2 ) INFORMATION FOR SEQ ID NO:145:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:145:

GGGAGGACGA UGCGGGUCUA UUGGGUAGGU GUUUGCAAGA AUUCCGCACG        50

AUAGGUAAAA CAGUGCAGAC GACTCGCCCG A        81

( 2 ) INFORMATION FOR SEQ ID NO:146:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH$_2$ cytosine ( i x ) FEATURE:
( D ) OTHER INFORMATION: All U'S are 2'-NH$_2$ uracil ( x i ) SEQUENCE DESCRIPTION: SEQ ID NO:146:

GGGAGGACGA UGCGGUGUAG GGGAAGUACG AGAGUGGGAG CGGCCGUAUA        50

GGUGGGAGUG UGCUCAGACG ACTCGCCCGA        80

( 2 ) INFORMATION FOR SEQ ID NO:147:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i x ) FEATURE:
( A ) NAME/KEY: modified base
( B ) LOCATION: 2..4, 15, 17..18
( D ) OTHER INFORMATION: C at positions 2-4, 15, 17-18
are 2'NH$_2$ cytosine ( i x ) FEATURE:
( A ) NAME/KEY: modified base
( B ) LOCATION: 5, 8, 11, 23
( D ) OTHER INFORMATION: U at positions 5, 8, 11, 23 are
2'NH$_2$ uracil ( x i ) SEQUENCE DESCRIPTION: SEQ ID NO:147:

ACCCUGAUGG UAGACGCCGG GGUG          24

(2) INFORMATION FOR SEQ ID NO:148:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: modified base
        (B) LOCATION: 2..4, 15, 17..18
        (D) OTHER INFORMATION: C at positions 2-4, 15, 17-18
            are 2'NH$_2$ cytosine (ix) FEATURE:
        (A) NAME/KEY: modified base
        (B) LOCATION: 5, 8, 11, 23
        (D) OTHER INFORMATION: U at positions 5, 8, 11 and 23
            are 2'NH$_2$ uracil (ix) FEATURE:
        (A) NAME/KEY: modified base
        (B) LOCATION: 12, 14
        (D) OTHER INFORMATION: A at positions 12 and 14 are
            2'OMe adenosine (ix) FEATURE:
        (A) NAME/KEY: modified base
        (B) LOCATION: 13, 16, 19..21, 22, 24
        (D) OTHER INFORMATION: G at positions 13, 16, 19-21, 22
            and 24 are 2'OMe guanosine (xi) SEQUENCE DESCRIPTION: SEQ ID NO:148:

ACCCUGAUGG UAGACGCCGG GGUG          24

(2) INFORMATION FOR SEQ ID NO:149:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified base
        (B) LOCATION: 6..8, 19, 21..22
        (D) OTHER INFORMATION: C at positions 6-8, 19 and 21-
            22 are 2'NH$_2$ cytosine (ix) FEATURE:
        (A) NAME/KEY: modified base
        (B) LOCATION: 9, 12, 15, 27
        (D) OTHER INFORMATION: U at positions 9, 12, 15 and 27
            are 2'NH$_2$ uracil (ix) FEATURE:
        (A) NAME/KEY: modified base
        (B) LOCATION: 1..4, 29..33
        (D) OTHER INFORMATION: T at positions 1-4 and 29-33 are
            2' deoxy phosphorothioate thymidine (xi) SEQUENCE DESCRIPTION: SEQ ID NO:149:

TTTTACCCUG AUGGUAGACG CCGGGGUGTT TTT          33

(2) INFORMATION FOR SEQ ID NO:150:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:

(D) OTHER INFORMATION: All A's, C's, G's, T's are 2'
deoxy- nucleotide derivatives (ix) FEATURE:
(A) NAME/KEY: modified base
(B) LOCATION: 1..4, 29..33
(D) OTHER INFORMATION: T at positions 1-4 and 29-33 are
phosphorothioate thymidine (xi) SEQUENCE DESCRIPTION: SEQ ID NO:150:

TTTTACCCTG ATGGTAGACG TTGGGGTGTT TTT    33

(2) INFORMATION FOR SEQ ID NO:151:

(i) SEQUENCE CHARACTERISTICS:
(A) LENGTH: 33 base pairs
(B) TYPE: nucleic acid
(C) STRANDEDNESS: single
(D) TOPOLOGY: linear (ix) FEATURE:
(D) OTHER INFORMATION: All A's, C's, G's, U's are
2'OMe- nucleotide derivatives (ix) FEATURE:
(A) NAME/KEY: modified base
(B) LOCATION: 1..4, 29..33
(D) OTHER INFORMATION: T's at positions 1-4 and 29-33
are 2' deoxy phosphorothioate thymidine (xi) SEQUENCE DESCRIPTION: SEQ ID NO:151:

TTTTACCCUG AUGGUAGACG CCGGGGUGTT TTT    33

(2) INFORMATION FOR SEQ ID NO:152:

(i) SEQUENCE CHARACTERISTICS:
(A) LENGTH: 33 base pairs
(B) TYPE: nucleic acid
(C) STRANDEDNESS: single
(D) TOPOLOGY: linear (ix) FEATURE:
(A) NAME/KEY: modified base
(B) LOCATION: 6..8, 19, 21..22
(D) OTHER INFORMATION: C at positions 6-8, 19 and 21-
22 are 2'$NH_2$ cytosine (ix) FEATURE:
(A) NAME/KEY: modified base
(B) LOCATION: 9, 12, 15, 27
(D) OTHER INFORMATION: U at positions 9, 12, 15 and 27
are 2'$NH_2$ uracil (ix) FEATURE:
(A) NAME/KEY: modified base
(B) LOCATION: 5, 16
(D) OTHER INFORMATION: A at positions 5 and 16 are
2'OMe adenine (ix) FEATURE:
(A) NAME/KEY: modified base
(B) LOCATION: 13, 17, 20, 23..26, 28
(D) OTHER INFORMATION: G at positions 13, 17, 20, 23-26
and 28 are 2'OMe guanosine (ix) FEATURE:
(A) NAME/KEY: modified base
(B) LOCATION: 1..4, 29..33
(D) OTHER INFORMATION: T's at positions 1-4 and 29-33
are 2' deoxy phosphorothioate thymidine (xi) SEQUENCE DESCRIPTION: SEQ ID NO:152:

TTTTACCCUG AUGGUAGACG CCGGGGUGTT TTT    33

( 2 ) INFORMATION FOR SEQ ID NO:153:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i x ) FEATURE:
( A ) NAME/KEY: modified base
( B ) LOCATION: 6..8, 19, 21..22
( D ) OTHER INFORMATION: C at positions 6-8, 19 and 21-22 are 2'NH$_2$ cytosine ( i x ) FEATURE:
( A ) NAME/KEY: modified base
( B ) LOCATION: 5, 8, 11, 23
( D ) OTHER INFORMATION: U at positions 9, 12, 15 and 27 are 2'NH$_2$ uracil ( i x ) FEATURE:
( A ) NAME/KEY: modified base
( B ) LOCATION: 5, 16
( D ) OTHER INFORMATION: A at positions 5 and 16 are 2'OMe adenine ( i x ) FEATURE:
( A ) NAME/KEY: modified base
( B ) LOCATION: 13, 17, 20, 24..26, 28
( D ) OTHER INFORMATION: G at positions 13, 17, 20, 24-26 and 28 are 2'OMe guanosine ( i x ) FEATURE:
( A ) NAME/KEY: modified base
( B ) LOCATION: 1..4, 29..33
( D ) OTHER INFORMATION: T's at positions 1-4 and 29-33 are 2' deoxy phosphorothioate thymidine ( x i ) SEQUENCE DESCRIPTION: SEQ ID NO:153:

TTTTACCCUG AUGGUAGACG CCGGGGUGTT TTT                    33

( 2 ) INFORMATION FOR SEQ ID NO:154:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i x ) FEATURE:
( A ) NAME/KEY: modified base
( B ) LOCATION: 6..8, 19, 21..22
( D ) OTHER INFORMATION: C at positions 6-8, 19 and 21-22 are 2'NH$_2$ cytosine ( i x ) FEATURE:
( A ) NAME/KEY: modified base
( B ) LOCATION: 9, 12, 15, 27
( D ) OTHER INFORMATION: U at positions 9, 12, 15 and 27 are 2'NH$_2$ uracil ( i x ) FEATURE:
( A ) NAME/KEY: modified base
( B ) LOCATION: 5, 16
( D ) OTHER INFORMATION: A at positions 5 and 16 are 2'OMe adenine ( i x ) FEATURE:
( A ) NAME/KEY: modified base
( B ) LOCATION: 13, 17, 20, 23..26, 28
( D ) OTHER INFORMATION: G at positions 13, 17, 20, 23-26 and 28 are 2'OMe guanosine ( i x ) FEATURE:
( A ) NAME/KEY: modified base
( B ) LOCATION: 11
( D ) OTHER INFORMATION: A at position 11 is phosphorothioate adenine ( i x ) FEATURE:
    ( A ) NAME/KEY: modified base
    ( B ) LOCATION: 1..4, 29..33
    ( D ) OTHER INFORMATION: T's at positions 1-4 and 29-33
      are 2' deoxy phosphorothioate thymidine ( x i ) SEQUENCE DESCRIPTION: SEQ ID NO:154:

TTTTACCCUG AUGGUAGACG CCGGGGUGTT TTT      33

( 2 ) INFORMATION FOR SEQ ID NO:155:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i x ) FEATURE:
    ( A ) NAME/KEY: modified base
    ( B ) LOCATION: 2..4, 15, 17..18
    ( D ) OTHER INFORMATION: C at positions 2-4, 15 and 17-
      18 are 2'NH$_2$ cytosine ( i x ) FEATURE:
    ( A ) NAME/KEY: modified base
    ( B ) LOCATION: 5, 8, 11, 23
    ( D ) OTHER INFORMATION: U at positions 5, 8, 11 and 23
      are 2'NH$_2$ uracil ( i x ) FEATURE:
    ( A ) NAME/KEY: modified base
    ( B ) LOCATION: 9
    ( D ) OTHER INFORMATION: G at position 9 is a 2:1 mixture
      of 2'OMe guanosine and 2'OH guanosine ( i x ) FEATURE:
    ( A ) NAME/KEY: modified base
    ( B ) LOCATION: 12, 14
    ( D ) OTHER INFORMATION: A at positions 12 and 14 are a
      2:1 mixture of 2'OMe adenine and 2'OH adenine ( x i ) SEQUENCE DESCRIPTION: SEQ ID NO:155:

ACCCUGAUGG UAGACGCCGG GGUG      24

( 2 ) INFORMATION FOR SEQ ID NO:156:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i x ) FEATURE:
    ( A ) NAME/KEY: modified base
    ( B ) LOCATION: 2..4, 15, 17..18
    ( D ) OTHER INFORMATION: C at positions 2-4, 15 and 17-
      18 are 2'NH$_2$ cytosine ( i x ) FEATURE:
    ( A ) NAME/KEY: modified base
    ( B ) LOCATION: 5, 8, 11, 23
    ( D ) OTHER INFORMATION: U at positions 5, 8, 11 and 23
      are 2'NH$_2$ uracil ( i x ) FEATURE:
    ( A ) NAME/KEY: modified base
    ( B ) LOCATION: 1, 7
    ( D ) OTHER INFORMATION: A at positions 1 and 7 are a 2:1
      mixture of 2'OMe adenine and 2'OH adenine ( i x ) FEATURE:
    ( A ) NAME/KEY: modified base
    ( B ) LOCATION: 19, 21
    ( D ) OTHER INFORMATION: G at positions 19 and 21 are a
      2:1 mixture of 2'OMe guanosine and 2'OH guanosine ( x i ) SEQUENCE DESCRIPTION: SEQ ID NO:156:

ACCCUGAUGG UAGACGCCGG GGUG  24

( 2 ) INFORMATION FOR SEQ ID NO:157:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i x ) FEATURE:
        ( A ) NAME/KEY: modified base
        ( B ) LOCATION: 2..4, 15, 17..18
        ( D ) OTHER INFORMATION: C at positions 2-4, 15 and 17-
            18 are 2'NH$_2$ cytosine ( i x ) FEATURE:
        ( A ) NAME/KEY: modified base
        ( B ) LOCATION: 5, 8, 11, 23
        ( D ) OTHER INFORMATION: U at positions 5, 8, 11 and 23
            are 2'NH$_2$ uracil ( i x ) FEATURE:
        ( A ) NAME/KEY: modified base
        ( B ) LOCATION: 6, 20, 24
        ( D ) OTHER INFORMATION: G at positions 6, 20, and 24 are
            a 2:1 mixture of 2'OMe guanosine and 2'OH guanosine ( x i ) SEQUENCE DESCRIPTION: SEQ ID NO:157:

ACCCUGAUGG UAGACGCCGG GGUG  24

( 2 ) INFORMATION FOR SEQ ID NO:158:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i x ) FEATURE:
        ( A ) NAME/KEY: modified base
        ( B ) LOCATION: 2..4, 15, 17..18
        ( D ) OTHER INFORMATION: C at positions 2-4, 15 and 17-
            18 are 2'NH$_2$ cytosine ( i x ) FEATURE:
        ( A ) NAME/KEY: modified base
        ( B ) LOCATION: 5, 8, 11, 23
        ( D ) OTHER INFORMATION: U at positions 5, 8, 11 and 23
            are 2'NH$_2$ uracil ( i x ) FEATURE:
        ( A ) NAME/KEY: modified base
        ( B ) LOCATION: 10, 13, 16
        ( D ) OTHER INFORMATION: G at positions 10, 13 and 16 are
            a 2:1 mixture of 2'OMe guanosine and 2'OH guanosine ( x i ) SEQUENCE DESCRIPTION: SEQ ID NO:158:

ACCCUGAUGG UAGACGCCGG GGUG  24

( 2 ) INFORMATION FOR SEQ ID NO:159:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

ATCCGCCTGA TTAGCGATAC TACAACGGCG TGGAAGACTA GAGTGCAGCC  50

GAACGCATCT AACTTGAGCA AAATCACCTG CAGGGG  86

( 2 ) INFORMATION FOR SEQ ID NO:160:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

ATCCGCCTGA TTAGCGATAC TACGCTACAA GTCCGCTGTG GTAGACAAGA  50

GTGCAGGCAA GACTTGAGCA AAATCACCTG CAGGGG  86

( 2 ) INFORMATION FOR SEQ ID NO:161:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:161:

ATCCGCCTGA TTAGCGATAC TAGGCCCGTC GAAGNTAGAG CGCAGGGCCC  50

CAAAATACCG ACTTGAGCAA AATCACCTGC AGGGG  85

( 2 ) INFORMATION FOR SEQ ID NO:162:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:162:

ATCCGCCTGA TTAGCGATAC TGTACCATCC ACGGTTTACG TGGACAAGAG  50

GGCCCTGGTA CACTTGAGCA AAATCACCTG CAGGGG  86

( 2 ) INFORMATION FOR SEQ ID NO:163:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:163:

ATCCGCCTGA TTAGCGATAC TTCACTACAA GTCCGCCGTG GTAGACAAGA  50

GTGCAGGCAA GACTTGAGCA AAATCACCTG CAGGGG  86

( 2 ) INFORMATION FOR SEQ ID NO:164:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:164:

ATCCGCCTGA TTAGCGATAC TACCGCTGTG TAGTTCCTTT AGGACTAGAG  50

GGCCGCCTAC ACTTGAGCAA AATCACCTGC AGGGG  85

( 2 ) INFORMATION FOR SEQ ID NO:165:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:165:

ATCCGCCTGA TTAGCGATAC TTAGGCTTGA CGTCTTCTAG ACTAGAGTGC    50

AGTCAAACCC ACTTGAGCAA AATCACCTGC AGGGG    85

( 2 ) INFORMATION FOR SEQ ID NO:166:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:166:

ATCCGCCTGA TTAGCGATAC TTGCAGGTCG ACTCTAGAGG ATCCCCGGGT    50

ACCGAGCTCG AACTTGAGCA AAATCACCTG CAGGGG    86

( 2 ) INFORMATION FOR SEQ ID NO:167:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:167:

ATCCGCCTGA TTAGCGATAC TACGGTTTAC GTGGACAAGA GGGCCCTGGT    50

ACACTTGAGC AAAATCACCT GCAGGGG    77

( 2 ) INFORMATION FOR SEQ ID NO:168:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:168:

ATCCGCCTGA TTAGCGATAC TGGTGGACTA GAGGNCAGCA AACGATCCTT    50

GGTTCGCGTC CACTTGAGCA AAATCACCTG CAGGGG    86

( 2 ) INFORMATION FOR SEQ ID NO:169:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:169:

ATCCGCCTGA TTAGCGATAC TTCAAGCACT CCCGTCTTCC AGACAAGAGT    50

GCAGGGCCTC TACTTGAGCA AAATCACCTG CAGGGG    86

( 2 ) INFORMATION FOR SEQ ID NO:170:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:170:

ATCCGCCTGA TTAGCGATAC TCGTGATGGA CAAGAGGGCC CTATCCACCG   50

GATATCCGTC ACTTGAGCAA AATCACCTGC AGGGG   85

( 2 ) INFORMATION FOR SEQ ID NO:171:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:171:

ATCCGCCTGA TTAGCGATAC TCAAGCAGTG CCCGTCTTCC AGACAAGAGT   50

GCAGGCCTCT ACTTGAGCAA AATCACCTGC AGGGG   85

( 2 ) INFORMATION FOR SEQ ID NO:172:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:172:

ATCCGCCTGA TTAGCGATAC TTGATCCACC GTTTATAGTC CGTGGTAGAC   50

AAGAGTGCAG GACTTGAGCA AAATCACCTG CAGGGG   86

( 2 ) INFORMATION FOR SEQ ID NO:173:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:173:

ATCCGCCTGA TTAGCGATAC TAACACACAA GAGGACAGTT ACAGGTAACA   50

TCCGCTCAGG ACTTGAGCAA AATCACCTGC AGGGG   85

( 2 ) INFORMATION FOR SEQ ID NO:174:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

ATCCGCCTGA TTAGCGATAC TAGTGGCGTC TATAGACAAG AGTGCAGCCC   50

GAGTTTCAAC TTGAGCAAAA TCACCTGCAG GGG   83

( 2 ) INFORMATION FOR SEQ ID NO:175:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

ATCCGCCTGA TTAGCGATAC TCCACAAGAG GGCAGCAAGT GTACAACTAC   50

```
AGCGTCCGGA CTTGAGCAAA ATCACCTGCA GGGG                                    84
```

( 2 ) INFORMATION FOR SEQ ID NO:176:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

```
CTACCTACGA TCTGACTAGC GCAGGCCAC GTCTATTTAG ACTAGAGTGC                    50
AGTGGTTCGC TTACTCTCAT GTAGTTCCT                                          79
```

( 2 ) INFORMATION FOR SEQ ID NO:177:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

```
CTACCTACGA TCTGACTAGC ACGGTCCAAA GGTTTCCCAT CCGTGGACTA                   50
GAGGGCACGT GCTTAGCTTA CTCTCATGTA GTTCCT                                  86
```

( 2 ) INFORMATION FOR SEQ ID NO:178:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

```
CTACCTACGA TCTGACTAGC CCGTCGCGTG ACTATAACCA CACGCAGACT                   50
AGAGTGCAGG GCTTAGCTTA CTCTCATGTA GTTCCT                                  86
```

( 2 ) INFORMATION FOR SEQ ID NO:179:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

```
CTACCTACGA TCTGACTAGC CCGAATGGGG CTGCGACTGC AGTGGACGTC                   50
ACGTCGTTAG CTTACTCTCA TGTAGTTCCT                                         80
```

( 2 ) INFORMATION FOR SEQ ID NO:180:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

```
CTACCTACGA TCTGACTAGC ACGCAAGAGA GTCNCCGAAT GCAGTCTCAG                   50
CCGCTAACAG CTTACTCTCA TGTAGTTCCT                                         80
```

( 2 ) INFORMATION FOR SEQ ID NO:181:

( i ) SEQUENCE CHARACTERISTICS:
- ( A ) LENGTH: 84 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:181:

```
ATCCGCCTGA TTAGCGATAC TCANNNCACT GCAAGCAATT GTGGCCCAAA       50
GGGCTGAGTA CTTGAGCAAA ATCACCTGCA GGGG                        84
```

( 2 ) INFORMATION FOR SEQ ID NO:182:

( i ) SEQUENCE CHARACTERISTICS:
- ( A ) LENGTH: 86 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:182:

```
ATCCGCCTGA TTAGCGATAC TGCTCGCTTA CAAAAGGGAG CCACTGTAGC       50
CCAGACTGGA CACTTGAGCA AAATCACCTG CAGGGG                      86
```

( 2 ) INFORMATION FOR SEQ ID NO:183:

( i ) SEQUENCE CHARACTERISTICS:
- ( A ) LENGTH: 86 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:183:

```
ATCCGCCTGA TTAGCGATAC TGGTTATGGT GTGGTTCCGA ATGGTGGGCA       50
AAGTAACGCT TACTTGAGCA AAATCACCTG CAGGGG                      86
```

( 2 ) INFORMATION FOR SEQ ID NO:184:

( i ) SEQUENCE CHARACTERISTICS:
- ( A ) LENGTH: 85 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:184:

```
ATCCGCCTGA TTAGCGATAC TGCTTGTNGC TCCGAAGGGG CGCGTATCCA       50
AGGACGGTTC ACTTGAGCAA AATCACCTGC AGGGG                       85
```

( 2 ) INFORMATION FOR SEQ ID NO:185:

( i ) SEQUENCE CHARACTERISTICS:
- ( A ) LENGTH: 83 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:185:

```
ATCCGCCTGA TTAGCGATAC TTATGGAGTG GTTCCGAATG GTGGGCAAAG       50
TAACGCTTAC TTGAGCAAAA TCACCTGCAG GGG                         83
```

( 2 ) INFORMATION FOR SEQ ID NO:186:

( i ) SEQUENCE CHARACTERISTICS:
- ( A ) LENGTH: 86 base pairs
- ( B ) TYPE: nucleic acid
- ( C ) STRANDEDNESS: single
- ( D ) TOPOLOGY: linear ( x i ) SEQUENCE DESCRIPTION: SEQ ID NO:186:

CTACCTACGA TCTGACTAGC TGCNNGCGGG CGGTTCTCCG GATGGGACCA    50

TAAGGCTTTA GCTTAGCTTA CTCTCATGTA GTTCCT    86

( 2 ) INFORMATION FOR SEQ ID NO:187:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:187:

CTACCTACGA TCTGACTAGC ACAAGGGGTC CTGNNGAATG GGGGAATACG    50

CTAGCCGAAG CTTACTCTCA TGTAGTTCCT    80

( 2 ) INFORMATION FOR SEQ ID NO:188:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:188:

CTACCTACGA TCTGACTAGC AACACGAGCA TGTGGGGTCC CTTCCGAATG    50

GGGGGTACAG GCTTAGCTTA CTCTCATGTA GTTCCT    86

( 2 ) INFORMATION FOR SEQ ID NO:189:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:189:

CTACCTACGA TCTGACTAGC GAGGCATTAG GTCCGAATGG TAGTAATGCT    50

GTCGTGCCTT GCTTAGCTTA CTCTCATGTA GTTCCT    86

( 2 ) INFORMATION FOR SEQ ID NO:190:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: Linear ( x i ) SEQUENCE DESCRIPTION: SEQ ID NO:190:

CTACCTACGA TCTGACTAGC CCGAATGGGG CTGCGACTGC AGTGGACGTC    50

ACGTCGTTAG CTTACTCTCA TGTAGTTCCT    80

( 2 ) INFORMATION FOR SEQ ID NO:191:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:191:

CTACCTACGA TCTGACTAGC GAGGAGGTGC GTTGTCCGAA GGGGTCGTTA    50

```
GTCACCTCGT  GCTTAGCTTA  CTCTCATGTA  GTTCCT                              86
```

( 2 ) INFORMATION FOR SEQ ID NO:192:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:192:

```
CTACCTACGA  TCTGACTAGC  GCAAGGGGTC  CTGCCGAATG  GGGGAATACG              50
CTAGCCGAAA  GCTTACTCTC  ATGTAGTTCC  T                                   81
```

( 2 ) INFORMATION FOR SEQ ID NO:193:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:193:

```
CTACCTACGA  TCTGACTAGC  ATCCTTCCGA  ATGGGGAAA   TGGCGNCCCA              50
GCTTACTCTC  ATGTAGTTCC  T                                               71
```

( 2 ) INFORMATION FOR SEQ ID NO:194:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:194:

```
CTACCTACGA  TCTGACTAGC  ACGCAAGAGA  GGTCNCCGAA  TGGCAGTCTC              50
AGCCGCTAAC  AGCTTACTCT  CATGTAGTTC  CT                                  82
```

( 2 ) INFORMATION FOR SEQ ID NO:195:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:195:

```
CTACCTACGA  TCTGACTAGC  CACGATAATC  CTCCGAAAGC  GTTGTCCGAA              50
TGGGTCGTTA  GCTTAGCTTA  CTCTCATGTA  GTTCCT                              86
```

( 2 ) INFORMATION FOR SEQ ID NO:196:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

```
ATCCGCCTGA  TTAGCGATAC  TTATCACCCC  CACTGGATAG  AGCCGCAGCG              50
TGCCCCTACT  ACTTGAGCAA  AATCACCTGC  AGGGG                               85
```

( 2 ) INFORMATION FOR SEQ ID NO:197:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( x i ) SEQUENCE DESCRIPTION: SEQ ID NO:197:

ATCCGCCTGA TTAGCGATAC TGCCCACTGC ATAGAGGGAC GGTTGTTTCC        50

GCCCGGTGTT TACTTGAGCA AAATCACCTG CAGGGG        86

( 2 ) INFORMATION FOR SEQ ID NO:198:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( x i ) SEQUENCE DESCRIPTION: SEQ ID NO:198:

CTACCTACGA TCTGACTAGC GTGAAGGAGC CCCAACTGGA TAGAAGCTT        50

AAGGCGGTGT GCTTACTCTC ATGTAGTTCC T        81

( 2 ) INFORMATION FOR SEQ ID NO:199:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( x i ) SEQUENCE DESCRIPTION: SEQ ID NO:199:

CTACCTACGA TCTGACTAGC CCACCGCAGA GTGTTACACC CCATAGGAGA        50

AGTCCGGATG GCTTAGCTTA CTCTCATGTA GTTCCT        86

( 2 ) INFORMATION FOR SEQ ID NO:200:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( x i ) SEQUENCE DESCRIPTION: SEQ ID NO:200:

CTACCTACGA TCTGACTAGC CCACTGCATA GAGAGTCGCA AGACACGGTG        50

CTTTATTCNC CGCTTAGCTT ACTCTCATGT AGTTCCT        87

( 2 ) INFORMATION FOR SEQ ID NO:201:

( i ) SEQUENCE CHARACTERISTICS:
( A ) LENGTH: 85 base pairs
( B ) TYPE: nucleic acid
( C ) STRANDEDNESS: single
( D ) TOPOLOGY: linear ( x i ) SEQUENCE DESCRIPTION: SEQ ID NO:201:

CTACCTACGA TCTGACTAGC TGCCCACTG GATAGAGTAG GAGGCCTAGC        50

CGACACGGTG CTTAGCTTAC TCTCATGTAG TTCCT        85

( 2 ) INFORMATION FOR SEQ ID NO:202:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( x i ) SEQUENCE DESCRIPTION: SEQ ID NO:202:

CTACCTACGA TCTGACTAGC CGAGGTCCCC CACTGGATAG AGTTGTTGAA 50

ACAACGGTGC GCTTAGCTTA CTCTCATGTA GTTCCT 86

( 2 ) INFORMATION FOR SEQ ID NO:203:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

CTACCTACGA TCTGACTAGC AACACTTCCC CACTGGATAG AGGCCTTTCG 50

CAGAGCCGGT GCTTAGCTTA CTCTCATGTA GTTCCT 86

( 2 ) INFORMATION FOR SEQ ID NO:204:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

CTACCTACGA TCTGACTAGC CCACTGCATA GAGAACTGGA TCGACGGTCC 50

AAAGTTCGGT GCTTAGCTTA CTCTCATGTA GTTCCT 86

( 2 ) INFORMATION FOR SEQ ID NO:205:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

CTACCTACGA TCTGACTAGC CCACTGCATA GAGATACTGG ATTCGACNNN 50

CCAAAGTTTC GGTGCTTAGC TTACTCTCAT GTAGTTCCT 89

( 2 ) INFORMATION FOR SEQ ID NO:206:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

CTACCTACGA TCTGACTAGC CCACTGCAGA GAGTCAACCT TACGANGCCA 50

AGGTTGCGGT GCTTAGCTTA CTCTCATGTA GTTCCT 86

( 2 ) INFORMATION FOR SEQ ID NO:207:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

ATCCGCCTGA TTAGCGATAC TTCTGCGAGA GACCTACTGG AACGTTTTGT 50

GATATTCACA ACTTGAGCAA AATCACCTGC AGGGG            85

(2) INFORMATION FOR SEQ ID NO:208:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:208:

ATCCGCCTGA TTAGCGATAC TATACACCCG GCGGGCCTAC CGGATCGTTG            50

ATTTCTCTCC ACTTGAGCAA AATCACCTGC AGGGG            85

(2) INFORMATION FOR SEQ ID NO:209:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:209:

ATCCGCCTGA TTAGCGATAC TACGCCCCCT GAGACCTACC GGAATNTTNT            50

CGCTAGGCCT AACTTGAGCA AAATCACCTG CAGGGG            86

(2) INFORMATION FOR SEQ ID NO:210:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:210:

ATCCGCCTGA TTAGCGATAC TGGGCATCTA ACCCAGACCT ACCGGAACGT            50

TATCGCTTGT GACTTGAGCA AAATCACCTG CAGGGG            86

(2) INFORMATION FOR SEQ ID NO:211:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO:211:

ATCCGCCTGA TTAGCGATAC TGGTGTGAAC CAGACCTACN GGAACGTTAT            50

CGCTTGTGAC TTGAGCAAAA TCACCTGCAG GGG            83

(2) INFORMATION FOR SEQ ID NO:212:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:212:

ATCCGCCTGA TTAGCGATAC TCATCAGTAT TATATAACGG GAACCAACGG            50

CAAATGCTGA CACTTGAGCA AAATCACCTG CAGGGG            86

(2) INFORMATION FOR SEQ ID NO:213:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:213:

| | | | | | |
|---|---|---|---|---|---|
| ATCCGCCTGA | TTAGCGATAC | TTCCNNGGGA | GAATAGGGTT | AGTCGGAGAA | 5 0 |
| GTTAATCGCT | ACTTGAGCAA | AATCACCTGC | AGGGG | | 8 5 |

( 2 ) INFORMATION FOR SEQ ID NO:214:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:214:

| | | | | | |
|---|---|---|---|---|---|
| ATCCGCCTGA | TTAGCGATAC | TCGGGAACGT | GTGGTTACNC | GGCCTACTGG | 5 0 |
| ATTGTTTCCT | GACTTGAGCA | AAATCACCTG | CAGGGG | | 8 6 |

( 2 ) INFORMATION FOR SEQ ID NO:215:

( i ) SEQUENCE CHARACTERISTICS:
    ( A ) LENGTH: 81 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:215:

| | | | | | |
|---|---|---|---|---|---|
| ATCCGCCTGA | TTAGCGATAC | TGGTAGGTCC | GGTGTGAAAG | AGGTTCGCAT | 5 0 |
| CAGGTAACTT | GAGCAAAATC | ACCTGCAGGG | G | | 8 1 |

( 2 ) INFORMATION FOR SEQ ID NO:216:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:216:

| | | | | | |
|---|---|---|---|---|---|
| ATCCGCCTGA | TTAGCGATAC | TCCTCAGGCA | ACATAGTTGA | GCATCGTATC | 5 0 |
| GATCCTGGAG | ACTTGAGCAA | AATCACCTGC | AGGGG | | 8 5 |

( 2 ) INFORMATION FOR SEQ ID NO:217:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:217:

| | | | | | |
|---|---|---|---|---|---|
| ATCCGCCTGA | TTAGCGATAC | TTTGGCTTGA | GTCCCGGGAC | GCACTGTTGA | 5 0 |
| CAGTGGAGTA | CTTGAGCAAA | ATCACCTGCA | GGGG | | 8 4 |

( 2 ) INFORMATION FOR SEQ ID NO:218:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:218:

ATCCGCCTGA TTAGCGATAC TCAGCAGGTT AGTATAACGG GAACCAACGG         50

CAAATGCTGA CACTTGAGCA AAATCACCTG CAGGGG         86

( 2 ) INFORMATION FOR SEQ ID NO:219:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

CTACCTACGA TCTGACTAGC GCAAGGGCAT CTCGGAATCG GTTAATCTGA         50

CTTGCAATAC GCTTAGCTTA CTCTCATGTA GTTCCT         86

( 2 ) INFORMATION FOR SEQ ID NO:220:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

CTACCTACGA TCTGACTAGC GATCCACGAA GAAGCTTACT CTCATGTAGT         50

TCCAGCTTAC TCTCATGTAG TTCCT         75

( 2 ) INFORMATION FOR SEQ ID NO:221:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

GTACCATCCA CGGTTTACGT GGACAAGAGG GCCCTGGTAC         40

( 2 ) INFORMATION FOR SEQ ID NO:222:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

GTAGTTCCTT TAGGACTAGA GGGCCGCCTA C         31

( 2 ) INFORMATION FOR SEQ ID NO:223:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

TGGACTAGAG GNCAGCAAAC GATCCTTGGT TCGCGTCC         38

( 2 ) INFORMATION FOR SEQ ID NO:224:

( i ) SEQUENCE CHARACTERISTICS:

(A) LENGTH: 26 base pairs
        (B) TYPE: nucleic acid
        (C) STRANDEDNESS: single
        (D) TOPOLOGY: linear (x i) SEQUENCE DESCRIPTION: SEQ ID NO:224:

CCCGTCTTCC AGACAAGAGT GCAGGG 26

(2) INFORMATION FOR SEQ ID NO:225:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:225:

AGGGCCACGT CTATTTAGAC TAGAGTGCAG TGGTTC 36

(2) INFORMATION FOR SEQ ID NO:226:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:226:

GGAGGTGCGT TGTCCGAAGG GGTCGTTAGT CACCTC 36

(2) INFORMATION FOR SEQ ID NO:227:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (x i) SEQUENCE DESCRIPTION: SEQ ID NO:227:

GCAAGGGGTC CTGCCGAATG GGGGAATACG CTAGCCGAAA 40

(2) INFORMATION FOR SEQ ID NO:228:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (x i) SEQUENCE DESCRIPTION: SEQ ID NO:228:

CGAGGTCCCC CACTGGATAG AGTTGTTGAA ACAACGGTGC GCTTA 45

(2) INFORMATION FOR SEQ ID NO:229:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (x i) SEQUENCE DESCRIPTION: SEQ ID NO:229:

AACACTTCCC CACTGGATAG AGGCCTTTCG CAGAGCCGGT GCTTA 45

(2) INFORMATION FOR SEQ ID NO:230:

(i) SEQUENCE CHARACTERISTICS:
        (A) LENGTH: 40 base pairs
        (B) TYPE: nucleic acid ( C ) STRANDEDNESS: single
( D ) TOPOLOGY: linear ( x i ) SEQUENCE DESCRIPTION: SEQ ID NO:230:

GGGCATCTAA CCCAGACCTA CCGGAACGTT ATCGCTTGTG 40

( 2 ) INFORMATION FOR SEQ ID NO:231:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:231:

AGACAAGAGT GCAGG 15

( 2 ) INFORMATION FOR SEQ ID NO:232:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:232:

GGACTAGAGG GCAGT 15

( 2 ) INFORMATION FOR SEQ ID NO:233:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:233:

CTCCGAATGG GGGNAAAG 18

( 2 ) INFORMATION FOR SEQ ID NO:234:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:234:

CCCCACTGGA TAGAG 15

( 2 ) INFORMATION FOR SEQ ID NO:235:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:235:

CCCCACTGCA TAGAG 15

( 2 ) INFORMATION FOR SEQ ID NO:236:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:236:

AGACCTACCG GAACGTT                                                                                    17

( 2 ) INFORMATION FOR SEQ ID NO:237:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:237:

ATCCGCTGA TTAGCGATAC TNNNNNNNN NNNNNNNNN NNNNNNNNN                                                    50

NNNNNNNNN NACTTGAGCA AAATCACCTG CAGGGG                                                                86

( 2 ) INFORMATION FOR SEQ ID NO:238:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( A ) NAME/KEY: modified base
        ( B ) LOCATION: 1..3
        ( D ) OTHER INFORMATION: N at positions 1-3 is biotin ( x i ) SEQUENCE DESCRIPTION: SEQ ID NO:238:

NNNCCCCTGC AGGTGATTTT GCTCAAGT                                                                        28

( 2 ) INFORMATION FOR SEQ ID NO:239:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:239:

ATCCGCCTGA TTAGCGATAC T                                                                               21

( 2 ) INFORMATION FOR SEQ ID NO:240:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:240:

CTACCTACGA TCTGACTAGC NNNNNNNNN NNNNNNNNN NNNNNNNNN                                                   50

NNNNNNNNN GCTTACTCTC ATGTAGTTCC T                                                                     81

( 2 ) INFORMATION FOR SEQ ID NO:241:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i x ) FEATURE:
        ( A ) NAME/KEY: modified base
        ( B ) LOCATION: 2, 4
        ( D ) OTHER INFORMATION: N at positions 2 and 4 is biotin ( x i ) SEQUENCE DESCRIPTION: SEQ ID NO:241:

ANANAGGAAC TACATGAGAG TAAGC 25

( 2 ) INFORMATION FOR SEQ ID NO:242:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:242:

CTACCTACGA TCTGACTAGC 20

HIGH-AFFINITY OLIGONUCLEOTIDE LIGANDS TO VASCULAR ENDOTHELIAL GROWTH FACTOR (VEGF)

RELATED APPLICATIONS

This application is a Continuation-in-Part of U.S. patent application Ser. No. 07/714,131, filed Jun. 10, 1991, entitled Nucleic Acid Ligands, now U.S. Pat. No. 5,475,096, which is a Continuation-in-Part of U.S. patent application Ser. No. 07/536,428, filed Jun. 11, 1990, entitled Systematic Evolution of Ligands by Exponential Enrichment, now abandoned, U.S. patent application Ser. No. 07/964,624, filed Oct. 21, 1992 entitled Methods of Producing Nucleic Acid Ligands, now U.S. Pat. No. 5,496,938 U.S. patent application Ser. No. 08/205,515, filed Mar. 3, 1994, now abandoned and U.S. patent application Ser. No. 08/233,012, filed Apr. 25, 1994 entitled High-Affinity Oligonucleotide Ligands to Vascular Endothelial Growth Factor (VEGF).

FIELD OF THE INVENTION

Described herein are high affinity nucleic acid ligands to vascular endothelial growth factor (VEGF). The method utilized herein for identifying such nucleic acid ligands is called SELEX, an acronym for Systematic Evolution of Ligands by EXponential enrichment.

BACKGROUND OF THE INVENTION

Neovascularization or angiogenesis is the process in which sprouting new blood vessels are formed from the existing endothelium in response to external stimuli that signal inadequate blood supply. Angiogenesis is generally rare under normal physiological conditions but frequently accompanies certain pathological conditions such as psoriasis, rheumatoid arthritis, hemangioma, and solid tumor growth and metastasis (Folkman & Klagsbrun, 1987) Science 235:442–447; Kim et al., (1993) Nature 362:841–844). Several growth factors that are capable of inducing angiogenesis in vivo have been identified to date including basic and acidic fibroblast growth factors (aFGF, bFGF), transforming growth factors $\alpha$ and $\beta$ (TGF$\alpha$, TGF$\beta$), platelet derived growth factor (PDGF), angiogenin, platelet-derived endothelial cell growth factor (PD-ECGF), interleukin-8 (IL-8), and vascular endothelial growth factor (VEGF).

VEGF was originally purified from guinea pig ascites and tumor cell cultures as a factor that increases vascular permeability (Senger, D. R. et al. (1983), Science 219:983–985) and it has therefore also been referred to as vascular permeability factor (VPF). VEGF is a heat and acid-stable, disulfide-linked homodimer. Four isoforms have been described (121, 165, 189 and 206 amino acids, respectively) and are believed to be the result of alternative splicing of mRNA. Despite the presence of an identical N-terminal hydrophobic signal sequence in all molecular isoforms of VEGF, only the two lower molecular weight species are efficiently secreted (Ferrara, N. et al. (1991) J. Cell. Biochem. 47:211–218). The predominant VEGF isoform in most cells and tissues is the 165 amino acid species. Although VEGF is typically glycosylated, glycosylation is only required for efficient secretion but not for activity (Yeo, T-. K. et al. (1991) Biochem. Biophys. Res. Commun. 179:1568–1575; Peretz, D. et al. (1992) Biochem. Biophys. Res. Commun. 182:1340–1347). The amino acid sequence of VEGF is highly conserved across species and exhibits a modest but significant homology (18–20%) to PDGF A and B (Jakeman L. B. et al. (1992) J. Clin. Invest. 89:244–253; Ferrara et al. (1992) Endocrine Rev. 13:18–32).

Unlike other angiogenic growth factors, target cell specificity of VEGF is limited to vascular endothelial cells. The biological actions of VEGF are mediated through its interaction with specific cell-associated receptors which have been identified in the majority of tissues and organs (Jakeman, L. B. (1992) J. Clin. Invest. 89:244–253). Three high-affinity receptors for VEGF have been cloned to date: flt1, kdr/flk-1 and flt4 (Vaisman, N. et al. (1990) J. Biol. Chem. 265:19461–19466; de Vries, C. et al. (1992) Science 255:989–991; Galland, F. et al. (1993) Oncogene 8:1233–1240). These receptors belong to a family of transmembrane tyrosine kinases and bind VEGF with dissociation constants between $10^{-11}$M to $10^{-12}$M. Recent experiments have shown that binding of VEGF to its high-affinity receptors is significantly enhanced by heparin or cell surface-associated heparin-like molecules (Gitay-Goren, H. (1992) J. Biol. Chem. 267:6093–6098).

In addition to promoting the growth of vascular endothelial cells and inducing vascular leakage, VEGF is also known to induce the proteolytic enzymes interstitial collagenase, urokinase-type plasminogen activator (uPA) and tissue-type plasminogen activator (tPA) (Unemori E. et al. (1993) J. Biol. Chem. in press; Pepper, M. S. et al. (1992) Biochem. Biophys. Res. Commun. 181:902-). These enzymes are known to play a prominent role in angiogenesis-related extracellular matrix degradation.

As a secreted and specific mitogen for endothelial cells, VEGF may be one of the major angiogenesis inducers in vivo. Several recent observations have supported this notion. For example, the expression of VEGF and its receptors accompanies angiogenesis associated with (i) embryonic development (Breier, G. et al. (1992) Development 114:521–532), (ii) hormonally-regulated reproductive cycle and (iii) tumor growth (Dvorak, H. F. (1991) J. Exp. Med. 174:1275–1278; Shweiki, D. et al. (1992) Nature 359:843–845; Plate, K. H. et al. (1992) Nature 359:845–848). It is relevant to note that aggressive tumor growth is accompanied by the generation of necrotic areas where oxygen and nutrient supplies are inadequate. Oxygen deprivation (hypoxia) in tissues is a known angiogenesis stimulant. Interestingly, VEGF expression was found to be the highest in tumor cells facing the necrotic areas (Shweiki, D. et al. (1992) supra; Plate, K. H. et al. (1992) supra). It has therefore been suggested by these authors that VEGF plays a key role in hypoxia-induced angiogenesis.

Recent experiments with neutralizing monoclonal antibodies (MAbs) to VEGF have been especially meaningful for establishing that this growth factor is an important tumor angiogenesis inducer in vivo (Kim, K. J. et al. (1993) Nature 362:841–844). Immunocompromized (nude) mice injected with human rhabdomyosarcoma, glioblastoma or leiomyosarcoma cell lines rapidly develop tumors. Specific neutralizing MAb to VEGF were found to inhibit the growth of these tumors. The density of tumor vasculature was decreased in MAb-treated animals as compared to controls. The same MAb, on the other hand, had no effect on the growth rate of the tumor cells in vitro suggesting that the growth inhibition was not mediated at the cellular level and appears to be mediated by the 165-amino acid isoform of VEGF.

BRIEF SUMMARY OF THE INVENTION

Herein described is the isolation and characterization of binding properties of a set of high-affinity nucleic acid ligands to VEGF. RNA, modified RNA, and ssDNA ligands are provided by the present invention. These ligands were selected from an initial pool of about 10¹⁴ RNA or DNA molecules randomized at thirty or forty contiguous positions. The evolved RNA ligands shown in FIGS. 2A–F bind VEGF with affinities in the low nanomolar range.

Also included herein are modified RNA ligands to VEGF. Such modified RNA ligands may be prepared after the identification of 2'-OH RNA ligands or by performing SELEX using a candidate mixture of modified RNAs. For example, 2'-NH$_2$ pyrimidine RNA ligands to VEGF are described herein and the evolved ligands are shown in Table 9. Additionally post-SELEX modified RNA ligands are provided in Table 4.

Also included herein are ssDNA ligands to VEGF. The evolved ssDNA ligands are shown in Table 8.

The present invention includes the method of identifying nucleic acid ligands and ligand sequences to VEGF comprising:

a) contacting a candidate mixture of nucleic acids with VEGF, wherein nucleic acids having an increased affinity to VEGF relative to the candidate mixture may be partitioned from the remainder of the candidate mixture;

b) partitioning the increased affinity nucleic acids from the remainder of the candidate mixture, and c) amplifying the increased affinity nucleic acids, whereby nucleic acid ligands to VEGF may be identified.

BRIEF DESCRIPTION OF THE FIGURES

FIG. 1 shows the starting RNA and PCR primers used in the SELEX experiment described in Examples 1 and 2.

FIGS. 2A–F show the aligned sequences and predicted secondary structures for the six families (grouped by primary sequence homology) of RNA ligands to VEGF. Arrows underline the inverted repeats of the double stranded (stem) regions. Lowercase and uppercase letters are used to distinguish nucleotides in the constant and the evolved sequence regions, respectively. Positions are numbered consecutively starting (arbitrarily) with the evolved nucleotide closest to the 5' end of the shown window.

FIGS. 5A and B show the results of the determination of the 3'- and 5'-boundaries for a representative high-affinity VEGF ligand (ligand 12) (SEQ ID NO:50). The 3'-boundary determination (FIG. 5A) showing partially hydrolyzed 5'-end labeled RNA (lane 4), hydrolytic fragments retained on nitrocellulose filters following incubation of the partially hydrolyzed RNA with VEGF at 5 nM (lane 1), 0.5 nM (lane 2), or 0.125 nM (lane 3) and partial digest of the 5'-end labeled RNA with RNAse T$_1$ (lane 5) resolved on an 8% denaturing polyacrylamide gel. The 5'-boundary (FIG. 5B) was determined in an identical manner except that RNA radiolabeled at the 3'-end was used. Shown are RNase T$_1$ digest (lane 1), partial alkaline hydrolysis (lane 2), and hydrolytic fragments retained on nitrocellulose filters following incubation with VEGF at 5 nM (lane 3), 0.5 nM (lane 4), or 0.125 nM (lane 5). Arrows indicate the 3'- and the 5'-boundaries of the minimal ligand 12 (italicized).

FIG. 6 shows the Scotchard analysis of $^{125}$I-VEGF binding to HUVECS. Data points are averages of two determinations. Increasing concentrations of $^{125}$I-VEGF were incubated with 2×10⁵ cells in the presence or absence of 50-fold excess of unlabeled VEGF to determine the amount of total (○), specific (□) and non-specific (Δ) binding of $^{125}$I-VEGF as a function of free $^{125}$I-VEGF concentration (insert).

FIG. 7 shows the effect of random RNA (○) and representative high affinity RNA ligands 100t (SEQ ID NO:51) (family 1) (Δ) and 44t (SEQ ID NO:52) (family 2) (□) on binding of $^{125}$I-VEGF to cell-surface receptors as a function of RNA concentration. The inhibitory affect of high affinity ligands representing other sequence families is virtually identical to that of ligands 100t and 44t.

FIG. 8 shows the starting random RNAs for experiments A and B, and PCR primers used in identifying 2'-NH$_2$-RNA ligands to VEGF (Example 4).

FIGS. 9A–G show 2'-NH$_2$-RNA ligands to VEGF identified via the SELEX technology as described in Example 4.

DETAILED DESCRIPTION OF THE INVENTION

Figure 3C:
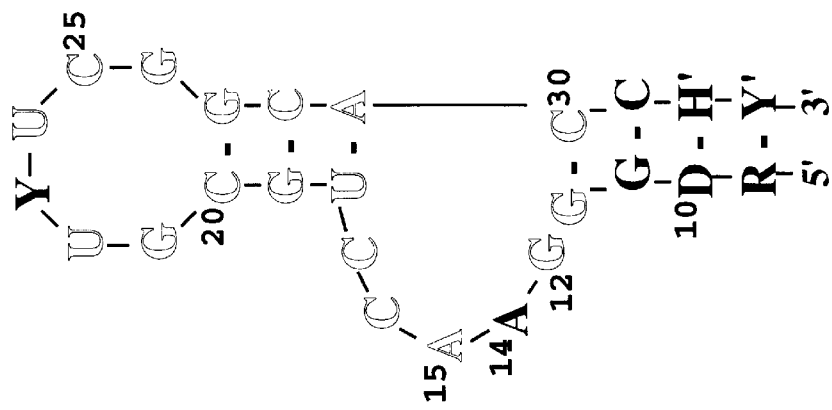
FIGS. 3A–F show the consensus sequences and predicted secondary structures for certain of the VEGF ligand families. Plain text is used to designate positions that occur at >60% but <80% frequencies. Positions where individual nucleotides are strongly conserved (frequencies >80%) are outlined. Residues in parenthesis occur at that position with equal frequencies to gaps. The numbering system described in the legend to FIG. 2 is used. R=A or G; Y=C or U; M=A or C; D=A, G or U; V=G, A or C; S=G or C; K=G or U; N=any base and prime (') indicates a complementary base.

This application describes high-affinity nucleic acid ligands to vascular endothelial growth factor (VEGF) identified through the method known as SELEX. The SELEX method is described in detail in U.S. patent application Ser. No. 07/536,428, filed Jun. 11, 1990, entitled Systematic Evolution of Ligands by EXponential Enrichment, now abandoned, U.S. patent application Ser. No. 07/714,131, filed Jun. 10, 1991, entitled Nucleic Acid Ligands, U.S. patent application Ser. No. 07/931,473, filed Aug. 17, 1992, entitled Nucleic Acid Ligands, now U.S. Pat. No. 5,270,163.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of vascular endothelial growth factor (VEGF). In the Example section below, the experimental parameters used to isolate and identify the nucleic acid ligand solutions to VEGF are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most situations it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. The '624 application, entitled Methods of Producing Nucleic Acid Ligands is specifically incorporated herein by reference.

This invention includes the specific RNA ligands to VEGF shown in FIGS. 2A–F (SEQ ID NOS:4–38). The scope of the ligands covered by this invention extends to all RNA ligands of VEGF identified according to the SELEX procedure. More specifically, this invention includes nucleic acid sequences that are substantially homologous to and that have substantially the same ability to bind VEGF as the specific nucleic acid ligands shown in FIGS. 2A–F. By substantially homologous it is meant a degree of primary sequence homology in excess of 70%, most preferably in excess of 80%. Substantially the same ability to bind VEGF means that the affinity is within one order of magnitude of the affinity of the ligands described herein. It is well within the skill of those of ordinary skill in the art to determine whether a given sequence—substantially homologous to those specifically described herein—has substantially the same ability to bind VEGF.

This invention also includes the 2'-NH$_2$ modified RNA ligands to VEGF as shown in FIGS. 9A–G. The scope of the present invention extends, therefore, to all modified nucleic acid ligands identified according to the SELEX method as well as to all sequences that are substantially homologous to and that have substantially the same ability to bind VEGF as ligands predicted in FIGS. 9A–G.

This invention also includes additional post-SELEX modified RNA ligands having 2'-O-methyl groups on various purine residues. In addition, nucleotides that contain phosphorothioate backbone linkages were added at the 5' and 3' ends of the ligands in order to reduce or prevent degradation by exonucleases. Internal backbone positions were also identified in which phosphorothioate linkages could be substituted, without the loss of binding affinity, to reduce or prevent endonucleolytic degradation. The post-SELEX modified RNA ligands provided in Table 4 (SEQ ID NOS:147–158) demonstrate an ability to inhibit the activity of exonucleases and endonucleases, without affecting binding affinities.

Further, this invention includes ssDNA ligands to VEGF. The specific ssDNA ligands are shown in Table 8 (SEQ ID NOS:159–230).

The scope of the ligands covered by this invention extends to all ssDNA ligands of VEGF identified according to the SELEX procedure. More specifically, this invention includes nucleic acid sequences that are substantially homologous to and that have substantially the same ability to bind VEGF as the specific nucleic acid ligands shown in Table 8. By substantially homologous it is meant a degree of primary sequence homology in excess of 70%, most preferably in excess of 80%. Substantially the same ability to bind VEGF means that the affinity is within one order of magnitude of the affinity of the ligands described herein. It is well within the skill of those of ordinary skill in the art to determine whether a given sequence—substantially homologous to those specifically described herein—has substantially the same ability to bind VEGF.

This invention encompasses the use of the disclosed ligands to identify a second ligand. In one embodiment, a first SELEX identified ligand which binds to a specific site of the target molecule is used to elute secondary ligands binding to the same site. In another embodiment, a first SELEX identified ligand binding to a specific site of the target molecule is used to select secondary ligands which do not bind to the same site. In this case, SELEX is conducted in the presence of the first ligand such that the binding site is saturated with the first ligand and selection occurs for ligands binding elsewhere on the target molecule. In a further embodiment analogous to the generation of anti-idiotype antibodies, a SELEX identified ligand to VEGF may itself be used as a target molecule to identify secondary ligands resembling the VEGF binding site. Such secondary ligands may compete with VEGF-substrate binding and inhibit the biological activity of VEGF.

A review of the sequence homologies of the nucleic acid ligands of VEGF shown in FIGS. 2A–F 9A–G and Table 8 shows that sequences with little or no primary homology may have substantially the same ability to bind VEGF. For these reasons, this invention also includes nucleic acid ligands that have substantially the same structure as the ligands presented herein and the substantially the same ability to bind VEGF as the nucleic acid ligands shown in FIGS. 2A–F and 9A–G and Table 8.

The following examples are provided to explain and illustrate the present invention and are not to be taken as limiting of the invention.

Example 1 describes the experimental procedures used to generate high-affinity nucleic acid ligands to VEGF. Example 2 describes the high-affinity RNA ligands to VEGF shown in FIGS. 2A–F. Example 3 describes the specificity of truncated RNA ligands to VEGF. Example 4 describes the experimental procedures used to generate 2'-NH$_2$ pyrimidine modified RNA ligands to VEGF. Example 5 describes post-SELEX modifications of VEGF RNA ligands with 2'-O-methyl groups on purines. Additionally, phosphorothioate backbone substitutions were made to reduce or prevent nuclease degradation without effecting binding affinity. Example 6 describes the stability of post-SELEX modified VEGF RNA ligands to ex vivo rat tissue degradation. Example 7 describes obtaining ssDNA ligands to VEGF.

EXAMPLE 1

EXPERIMENTAL PROCEDURES

Materials

Recombinant human VEGF (165 amino acid form; MW 46,000) was a generous gift from Dr. Napoleone Ferrara (Genentech). All other reagents and chemicals were of the highest purity available and were purchased from commercial sources.

SELEX

Essential features of the SELEX protocol have been described in detail in U.S. Pat. No. 5,270,163 as well as in previous papers from these laboratories (See, e.g., Schneider et al. (1992) J. Mol. Biol. 228:862). Briefly, DNA templates for in vitro transcription (that contain a region of thirty random positions flanked by constant sequence regions) and the corresponding PCR primers were prepared chemically using established solid phase oligonucleotide synthesis protocols.

The random region was generated by utilizing an equimolar mixture of the four unmodified nucleotides during oligonucleotide synthesis. The two constant regions were designed to contain PCR primer annealing sites, primer annealing site for cDNA synthesis, T7 RNA polymerase promoter region and restriction enzyme sites that allow cloning into vectors (FIG. 1) (SEQ ID NOS:1–3). An initial pool of RNA molecules was prepared by in vitro transcription of approximately 200 picomoles ($10^{14}$ molecules) of the double stranded DNA template utilizing T7 RNA polymerase. Transcription mixtures consisting of 100–300 nM template, 5 units/µl T7 RNA polymerase, 40 mM Tris-Cl buffer (pH 8.0) containing 12 mM MgCl$_2$, 5 mM DTT, 1 mM spermidine, 0.002% Triton X-100, 4% PEG were incubated at 37° C. for 2–3 hours. These conditions typically resulted in transcriptional amplification of 10 to 100-fold. Selections for high affinity RNA ligands were done by incubating bFGF with RNA for 10–20 minutes at 37° C. in 50 ml of phosphate buffered saline (PBS=10.1 mM Na$_2$HPO$_4$, 1.8 mM KH$_2$PO$_4$, 137 mM NaCl, 2.7 mM KCl, pH 7.4) and then separating the protein-RNA complexes from the unbound species by nitrocellulose filter partitioning (Tuerk, C. and Gold, L. (1990) Science 249:505–510). The selected RNA (which typically amounted to 5–10% of the total input RNA) was then extracted from the filters and reverse transcribed into cDNA by avian myeloblastoma virus reverse transcriptase (AMV RT). Reverse transcriptions were done at 48° C. (60 min) in 50 mM Tris buffer (pH 8.3), 60 mM NaCl, 6 mM Mg(OAc)2, 10 mM DTT and 1 unit/µl AMV RT. Amplification of the cDNA by PCR under standard conditions yielded a sufficient amount of double-stranded DNA for the next round of in vitro transcription.

Nitrocellulose Filter Binding Assays

Oligonucleotides bound to proteins can be effectively separated from the unbound species by filtration through nitrocellulose membrane filters (Yarus, M. and Berg, P. (1970) Anal. Biochem. 35:450–465; Lowary, P. T. and Uhlenbeck, O. C. (1987) Nucleic Acids Res. 15:10483–10493; Tuerk, C. and Gold, L. (1990) supra). Nitrocellulose filters (0.2 µm pore size, Schleicher and Schuell, Keene, N.H.) were secured on a filter manifold and washed with 4–10 ml of buffer. Following incubations of $^{32}$P labeled RNA with serial dilutions of the protein for 10 min at 37° C. in buffer (PBS) containing 0.01% human serum albumin (HSA), the solutions were applied to the filters under gentle vacuum in 45 ml aliquots and washed with 5 ml of PBS. The filters were than dried under an infrared lamp and counted in a scintillation counter.

Equilibrium Dissociation Constants

In the simplest case, equilibrium binding of RNA (R) to VEGF (P) can be described by eq. 1,

$$R \cdot P \underset{}{\overset{Kd}{\rightleftharpoons}} R + P \tag{1}$$

where Kd=([R][P]/[R.P]) is the equilibrium dissociation constant. Using the mass-balance equations, the fraction of bound RNA at equilibrium (q) can be expressed in terms of measurable quantities (eq. 2), $$q = (f/2Rt)\{Pt+Rt+Kd-[(Pt+Rt+Kd)^2-4PtRt]^{1/2}\} \tag{2}$$

where Pt and Rt are total protein and total RNA concentrations and f reflects the efficiency of retention of the protein-RNA complexes on nitrocellulose filters. The average value of f for VEGF in our assays was 0.7.

Most RNA ligands exhibited biphasic binding to VEGF. For those ligands, binding of RNA to VEGF is described by a model where total RNA is assumed to be partitioned between two non-interconverting components (R1 and R2) that bind to VEGF with different affinities (eqs 3 and 4).

$$R1 \cdot P \underset{}{\overset{Kd1}{\rightleftharpoons}} R1 + P \tag{3}$$

-continued

In this case, the fraction of total bound RNA (q) is given by eq. 5.

$$q=(f/2Rt)\{2Pt+Rt+Kd1+Kd2-[(Pt+\chi 1Rt+Kd1)^2-4Pt\chi 1Rt]^{1/2}-[(Pt+\chi 2Rt+Kd2)^2-4Pt\chi 2Rt]^{1/2}\} \quad (5)$$

where $\chi^1$ and $\chi^2$ (=1−c1) are the mole fractions of R1 and R2 and Kd1 and Kd2 are the corresponding dissociation constants.

Internally-labeled RNA ligands used for binding studies were prepared by in vitro transcription using T7 RNA polymerase (Milligan et al. (1987) Nucl. Acids Res. 15:8783) and were purified on denaturing polyacrylamide gels to ensure size homogeneity. All RNA ligands were diluted to about 1 nM in PBS, denatured at 90° C. for 2 minutes, and then cooled on ice prior to incubation with the protein. This denaturation/renaturation cycle performed at high dilution is necessary to ensure that the RNA is essentially free from dimers and other higher order aggregates. Concentrations of the stock solutions of VEGF, from which other dilutions were made, were determined from the absorbance reading at 280 nm using the calculated value for $\epsilon_{280}$ of 46,600 $M^{-1}cm^{-1}$ for the VEGF dimer (Gill et al. (1989) Anal. Biochem. 182:319). Data sets that define the binding curves were fit to either eq. 2 or eq. 5 by the non-linear least squares method using the software package Kaleidagraph (Synergy Software, Reading, Pa.).

Information Boundary Determinations

High-affinity VEGF ligands were radiolabeled at the 5'-end with γ-$^{32}$P-ATP (New England Biolabs, Beverly, Mass.) and T4 polynucleotide kinase (New England Biolabs, Beverly, Mass.) for the 3'-boundary determinations, or at the 3'-end with α$^{32}$pCp and T4 RNA ligase (New England Biolabs) for the 5'-boundary determination. Radiolabeled RNA ligands were subjected to partial alkaline hydrolysis and then selectively bound in solution to VEGF at 5, 0.5, or 0.125 nM before being passed through nitrocellulose filters. Retained oligonucleotides were resolved on 8% denaturing polyacrylamide gels. In each experiment, the smallest radiolabeled oligonucleotide bound by VEFG at the lowest protein concentration defines the information boundary. Partial digests of the 5'- or the 3'-labelled RNA ligands with RNAse $T_1$ (Boehringer Mannheim Biochemicals, Indianapolis, Ind.) were used to mark the positions of labeled oligonucleotides ending with a guanosine.

Cloning and Sequencing

Individual members of the enriched pool were cloned into pUC18 vector and sequenced as described (Schneider, D. et al. (1992) J. Mol. Biol. 228:862–869).

Receptor Binding

VEGF was radioiodinated by the Iodegen method (Jakeman et al. (1992) J. Clin. Invest. 89:244) to a specific activity of 2.4×10$^4$ cpm/ng. Human umbilical vein endothelial cells (HUVECs) were plated in 24-well plates at a density of 1–2×10$^5$ cells/well and grown to confluence in EGM (Clonetics, San Diego, Calif.) media (24–48 hrs). At confluence, the cells were washed 3 times with PBS and incubated for 2 hrs at 4° C. in α-MEM serum-free media containing $^{125}$I-labeled VEGF with or without unlabeled competitor (VEGF, EGF, or RNA). For experiments done with RNA, 0.2 units of placental RNase inhibitor (Promega, Madison, Wis.) were included in the media. It was determined that the RNA ligands were not degraded during the course of the experiment. At the end of the 2 hr incubation period, the supernatant was removed and the wells washed 2 times with PBS. HUVECs were then lysed with 1% triton X-100/1M NaOH and the amount of cell-associated $^{125}$I-VEGF determined by gamma counting.

EXAMPLE 2

RNA LIGANDS TO VEGF

Approximately 10$^{14}$ RNA molecules randomized at thirty contiguous positions (SEQ ID NO:1) were used in the initial selection targeting VEGF. Random RNA bound to VEGF with an affinity of approximately 0.2 μM. After 13 rounds of SELEX, the observed improvement in affinity of the evolved RNA pool was about two orders of magnitude (data not shown). 64 isolates were cloned and sequenced from this evolved pool, and 37 unique sequences found (sequences differing at only one or two positions were not considered unique). 34 of the 37 unique sequences could be classified into six families based on sequence similarity in the evolved region (FIGS. 2A–F) (SEQ ID NOS:4–38). The evolved sequence is provided in capitol letters in FIG. 2. Lower case letters indicate portions of the fixed sequence included in the alignment. The cloned sequence included both the evolved and fixed sequences. Three unique clones, 4 (GGGAUGUUUGGCUAUCUCGGAUAGUGCCCC) (SEQ ID NO:39), 16 (GCUUAAUACGACUCACUNUAGGGAGCUCAG) (SEQ ID NO:40) and 18 (UUGAGUGAUGUGCUUGACGUAUCGCUGCAC) (SEQ ID NO:41) had a more limited sequence similarity with members of the six families.

Consensus Structures

Figure 3B:
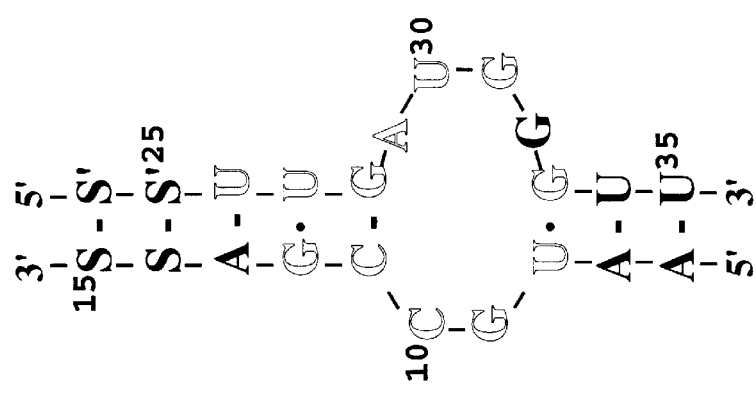
Figure 3A:
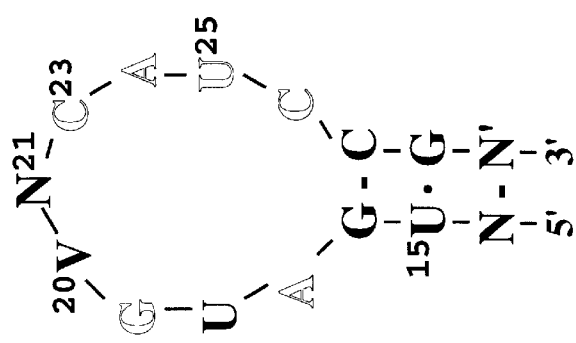
Figure 3F:
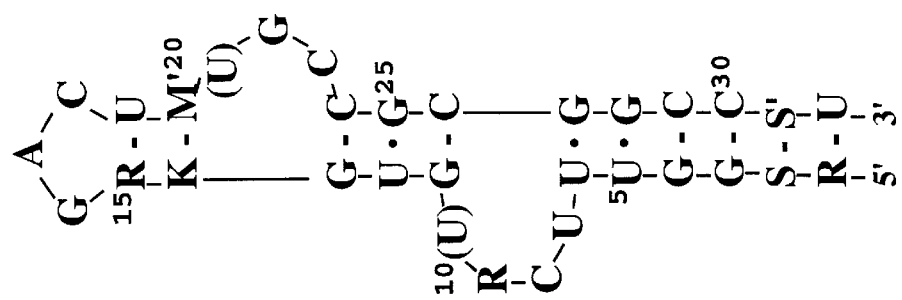
Figure 3E:
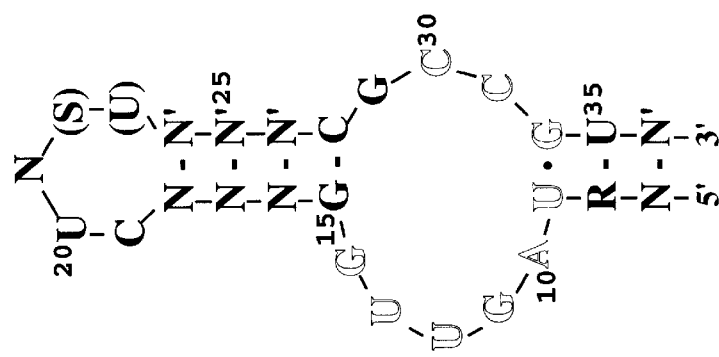
Figure 3D:
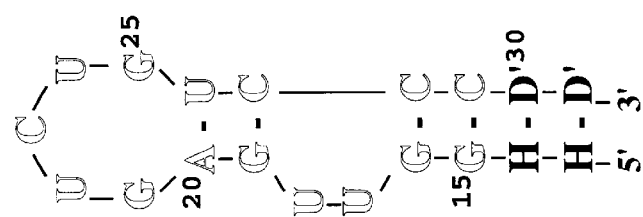

In addition to allowing determination of consensus primary structures, groups of similar sequences consisting of members that share a defined functional property often contain useful clues for secondary structure prediction (James et al. (1988) Meth. Enzymol. 180:227). The underlying assumption is that ligands with similar primary structures are capable of adopting similar secondary structures in which the conserved residues are organized in unique, well-defined motifs. In this context, ligands which have strong, unambiguous secondary structures can provide good structural leads for other sequences within a similar set where consensus folding may be less obvious. Conserved elements of secondary structure, such as base-pairing, may also be detected through covariation analysis of aligned sequence sets (James et al. (1988) supra; Gutell et al. (1992) Nucl. Acids Res. 20:5785). The predicted consensus secondary structures for the six sequence families are shown in FIGS. 3A–F (SEQ ID NOS:42–47).

The most highly conserved residues in the family 1 sequence set (A17, G19 and the CAUC sequence at positions 23–26) can be accommodated in the 9–10 nucleotide loop (SEQ ID NO:42). Base-pairing covariation between positions 16 and 27 (G-C occurs with a frequency of 8 out of 11 times (8/11) and C-G with a frequency of 3/11), positions 15 and 28 (U-G, 7/11; G-C, 3/11; U-A, 1/11) and positions 14 and 29 (G-C, 5/11; U-A, 2/11, and C-G, 1/11) supports the predicted secondary structure. It is worth noting that many ligands in this family have stable extended stems that contain up to 15 base pairs.

In the family 2 sequence set, the strongly conserved UGCCG and UUGAUG(G/U)G sequences (positions 8–12 and 26–33) are circularly permutated. In the consensus secondary structures, these nucleotides are found in an identical arrangement within or adjacent to the asymmetrical internal loop (FIGS. 3A–F) (SEQ ID NO:43). This result suggests that the nucleotides outside of the consensus motif shown in FIGS. 3A–F are unimportant for binding. Base-pairing covariation is noted between positions 5 and 36 (C-G, 2/7; G-C, 2/7; U-A, 1/7; G-U, 1/7), 6 and 35 (A-U, 4/7; C-G, 1/7; G-C, 1/7), 7 and 34 (A-U, 4/7; G-C, 1/7), 11 and 28 (C-G, 6/7; G-C, 1/7), 12 and 27 (G-U, 6/7; C-G, 1/7), 13 and 26 (A-U, 5/7; G-C, 1/7; G-U, 1/7), 14 and 25 (G-C, 4/7; C-G, 2/7) and 15 and 24 (C-G, 4/7; G-C, 2/7) .

Family 3 and family 4 sequence sets are characterized by highly conserved contiguous stretches of 21 (GGGAACCUGCGU(C/U)UCGGCACC (SEQ ID NO:48), positions 11–31) and 15 (GGUUGAGUCUGUCCC (SEQ ID NO:49), positions 15–29) arranged in bulged hairpin motifs (FIGS. 3C and D) (SEQ ID NOS:44–45). Base-pairing covariation is detected in family 3 between positions 8 and 33 (A-U, 2/4; G-C, 2/4), 9 and 32 (A-U, 2/4; U-A, 1/4; G-C, 1/4), and 10 and 31 (A-U, 1/4; G-C, 3/4) and in family 4 between positions 13 and 31 (A-U, 4/7; C-G, 2/7; U-A, 1/7) and 14 and 30 (C-G, 3/7; U-A, 3/7; A-U, 1/7).

Family 5 consensus secondary structure is an asymmetrical internal loop where the conserved UAGUUGG (positions 9–15) and CCG (positions 29–31) sequences are interrupted by less conserved sequences (FIGS. 3A–F) (SEQ ID NO:46). Modest base-pairing covariation is found between positions 8 and 32 (A-U, 2/4; U-G, 1/4), 16 and 26 (G-C, 2/4; A-U, 1/4), 17 and 25 (A-U, 2/4; G-C, 1/4) and 18 and 24 (C-G, 2/4; G-C, 1/4).

Family 6 has only two sequences and therefore the concept of consensus sequence or consensus structure is less meaningful. Nevertheless, the two sequences are very similar (90% identity) and can be folded into a common motif (FIG. 3F) (SEQ ID NO:47). Base-pairing covariation is found between positions 1 and 32 (A-U, 1/2; G-U, 1/2), 2 and 31 (C-G, 1/2; G-C, 1/2), 14 and 20 (U-A, 1/2; G-C, 1/2) and 15 and 19 (A-U, 1/2; G-U, 1/2).

Affinities

Figure 4A:
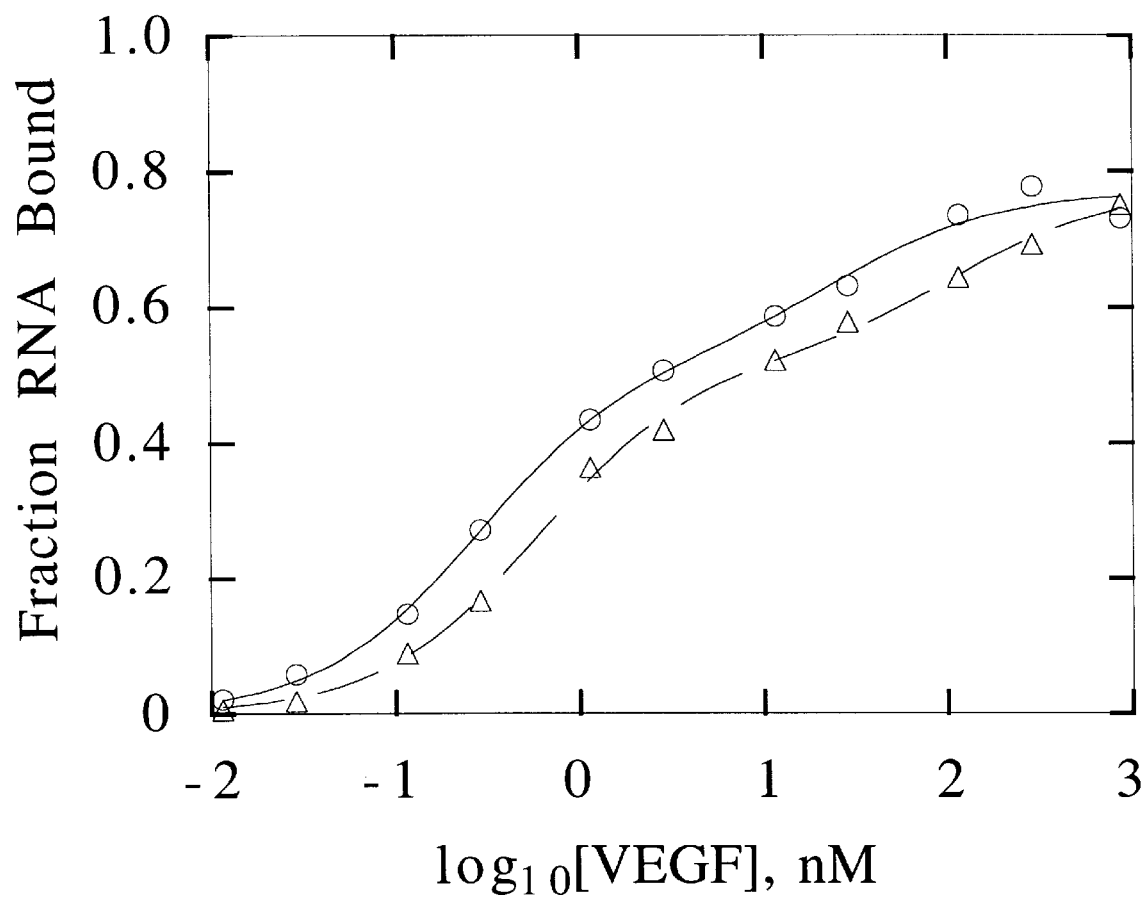
FIGS. 4A–F show the binding curves for a representative set of high-affinity ligands to VEGF. Full-length (○) and truncated (Δ) ligands tested were 100 (SEQ ID NO:11) and 100t (SEQ ID NO:51) (family 1, FIG. 4A), 44 (SEQ ID NO:20) and 44t (SEQ ID NO:52) (family 2, FIG. 4B), 12 (SEQ ID NO:22) and 12t (SEQ ID NO:53) (family 3, FIG. 4C), 40 (SEQ ID NO:28) and 40t (SEQ ID NO:54) (family 4, FIG. 4D), 84 (SEQ ID NO:36) and 84t (SEQ ID NO:55) (family 5, FIG. 4E), and 126 (SEQ ID NO:38) and 126t (SEQ ID NO:56) (family 6, FIG. 4F). The fraction of ³²P-labeled RNA bound to nitrocellulose filters is plotted as a function of total protein concentration and the lines represent the fit of the data points to eq. 2 (40t, 84 and 84t) or to eq. 5 (all other ligands). RNA concentrations were determined from their absorbance reading at 260 nm (and were typically <50 pM). Binding reactions were done at 37° C. in phosphate buffered saline containing 0.01% human serum albumin.
Figure 4B:
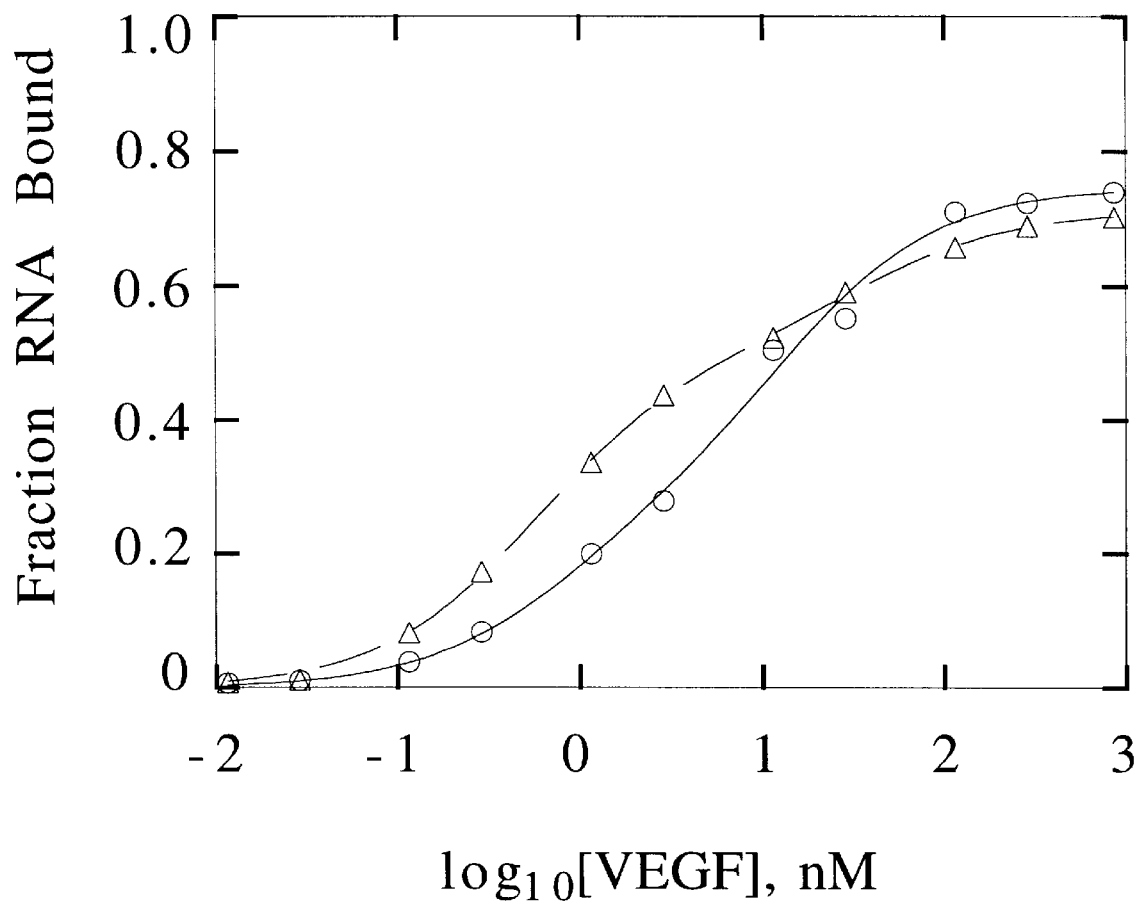
Figure 4C:
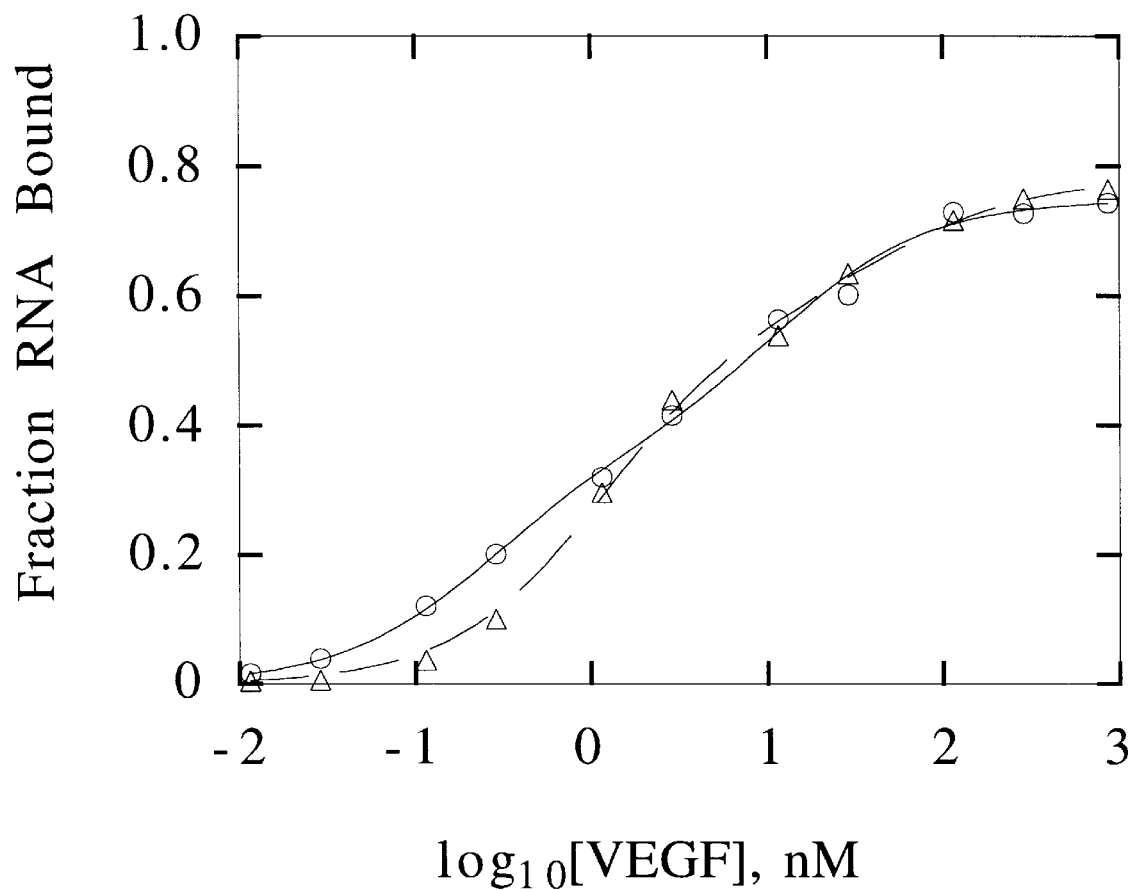
Figure 4D:
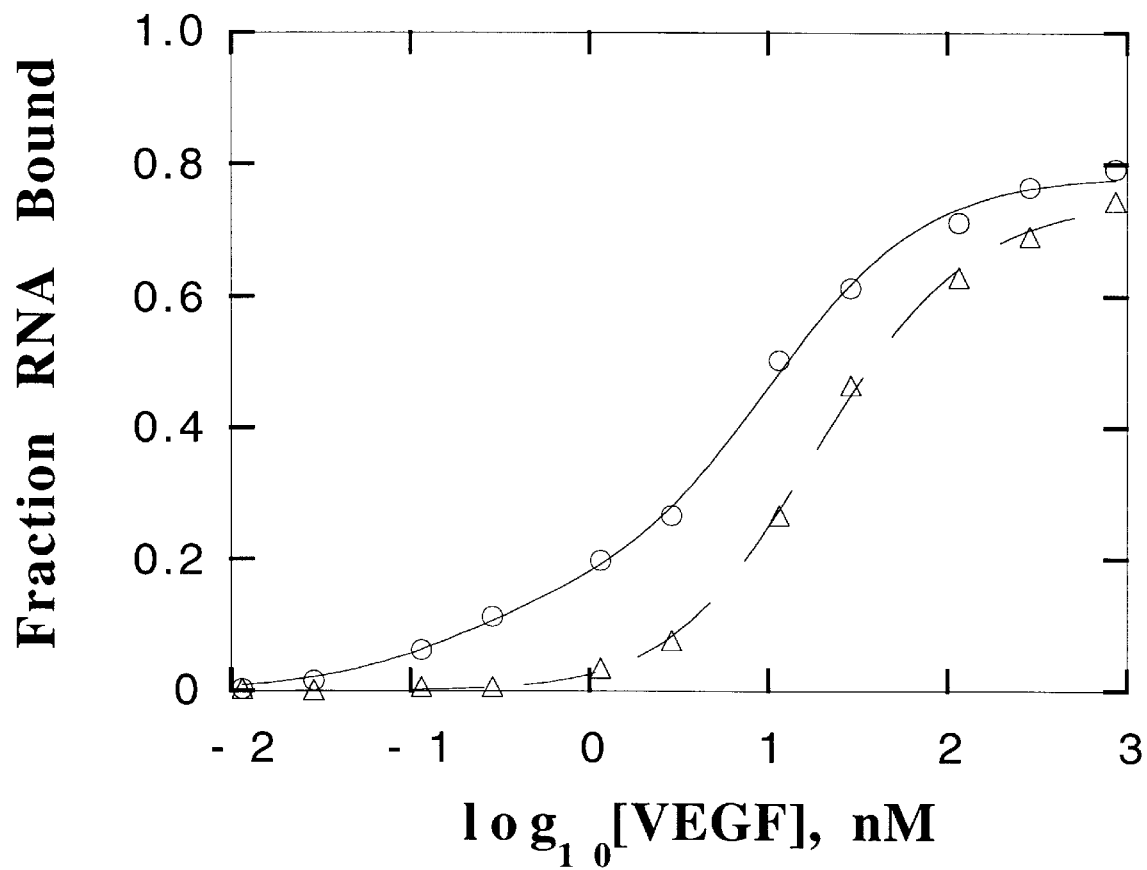
Figure 4E:
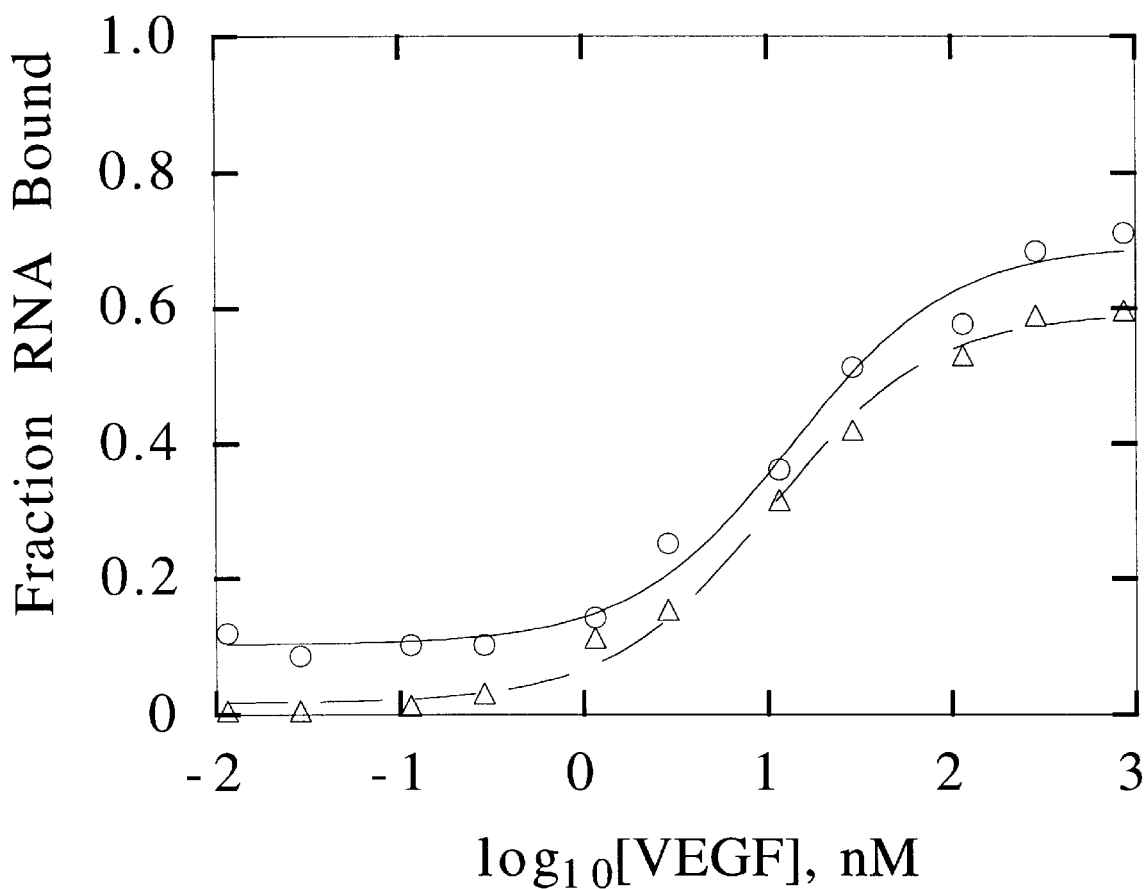
Figure 4F:
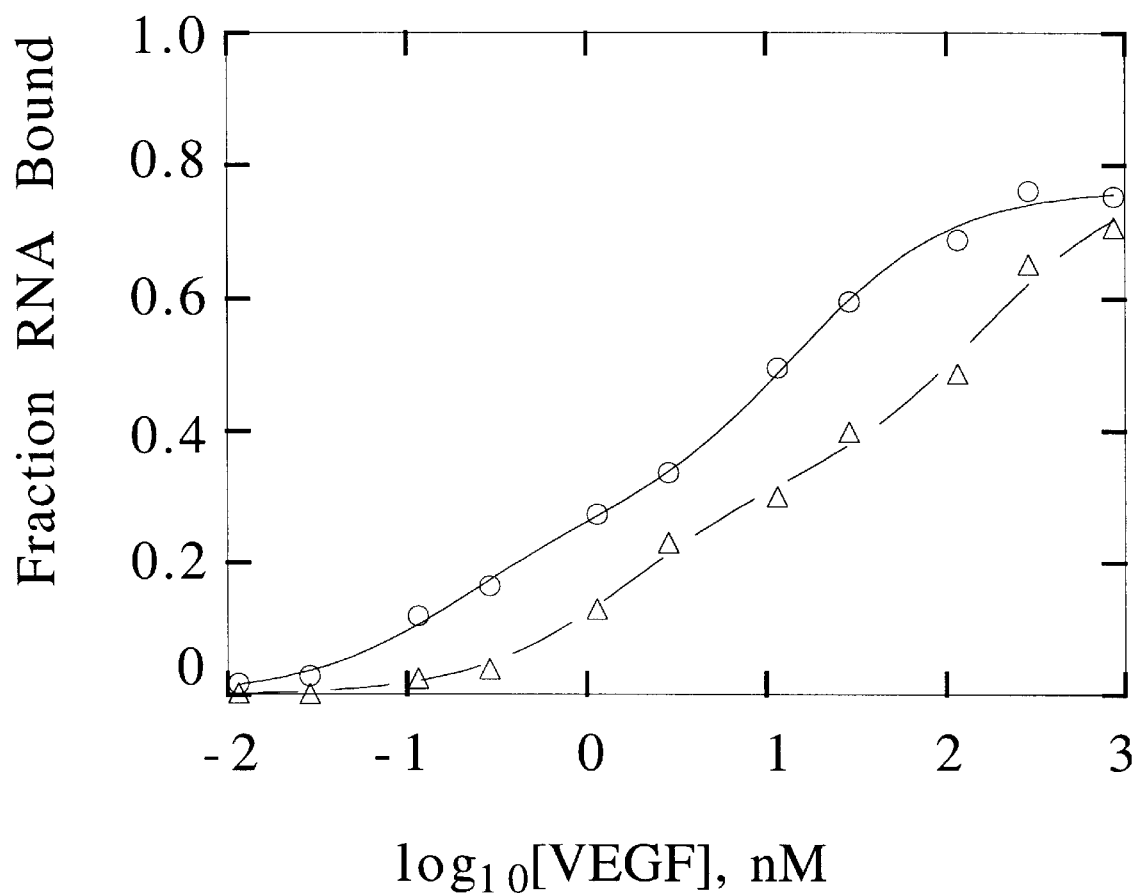

The affinity of all unique sequence clones for VEGF was screened by determining the amount of RNA bound to VEGF at two protein concentrations (1 and 10 nM). Binding of the best ligands from each of the six sequence families was then analyzed over a range of protein concentrations (FIGS. 4A–F). Dissociation constants were calculated by fitting the data points to either eq. 2 (monophasic binding) or eq. 5 (biphasic binding) and their values are shown in Table 1.

Information Boundaries

In order to determine the minimal sequence information necessary for high-affinity binding to VEGF, deletion analyses were performed with representative members from each of the six families. These experiments were done by radiolabeling RNA ligands at either the 3' end or the 5' end (for the 3' or the 5' boundary determinations, respectively) followed by limited alkaline hydrolysis, partitioning of the free and the bound RNA by nitrocellulose filtration and resolving the hydrolytic fragments that retained high affinity for VEGF on denaturing polyacrylamide gels (Tuerk et al. (1990) J. Mol. Biol. 213:749). The combined information from the 3' and the 5' boundary experiments outlines the shortest sequence segment that has high affinity for the protein (FIG. 5) (SEQ ID NO:50). It is important to realize that these experiments define boundaries sequentially at the unlabeled ends of ligands in the context of full-length labeled ends. Since the full-length ends may provide additional contacts with the protein or participate in competing secondary structures, ligands truncated at both ends may have lower or higher affinities for the protein than their full-length parent. The following truncated ligands were prepared by in vitro transcription from synthetic DNA templates: 100t (Family 1) GGCCGGUAGUCGCAUGGCCCAUCGCGCCCGG (SEQ ID NO:51), 44t (Family 2) GGaaGCU-UGAUGGGUGACACACGUCAUGCCGAGCu (SEQ ID NO:52), 12t (Family 3) GGAAGGGAACCUGCGUCUCG-GCACCuucg (SEQ ID NO:53), 40t (Family 4) GGU-CAACGGUUGAGUCUGUCCCGuucgac (SEQ ID NO:54), 84t (Family 5) GgcucaaUAGUUGGAGGCCU-GUCCUCGCCGUAGAGC (SEQ ID NO:55) and 126t (Family 6) GGaACGGUUCUGUGUGUGGACUAGC-CGCGGCCGuu (SEQ ID NO:56) (letter t designates truncated sequences; underlined guanines are not present in the original sequences and were added to increase the transcriptional efficiency (Milligan et al. (1990) supra); lowercase letters indicate nucleotides from the constant sequence region). Binding curves for these truncated ligands and their dissociation constants are shown alongside their parent ligands in FIG. 4 and Table 1. The dissociation constants of the truncated versus full-length ligands are generally comparable, although ligands 40t (SEQ ID NO:54) and 126t (SEQ ID NO:56) clearly bind to VEGF significantly less well than the corresponding full-length ligands.

Competition experiments revealed that binding of all possible pairwise combinations of truncated ligands representing each of the families is mutually exclusive (100t, 44t, 12t, 40t, 84t and 126t (SEQ ID NOS:51–56, respectively). Furthermore, all of these ligands are displaced by low-molecular weight (≅5,100 Da) heparin (data not shown). Truncated ligands and low-molecular weight heparin were used in these studies in order to maximize the probability of observing non-competing ligand pairs. It appears, therefore, that although there are multiple non-isomorphic solutions to high-affinity binding to VEGF, all examined ligands may bind to the same region of the protein. Proteins in general may have "immunodominant" domains for nucleic acid ligands.

EXAMPLE 3

SPECIFICITY OF TRUNCATED RNA LIGANDS TO VEGF

Binding of two truncated high-affinity ligands, 100t and 44t (SEQ ID NOS:51–52), to four other heparin binding proteins (bFGF, PDGF, antithrombin III and thrombin) was tested in order to address the question of specificity. Dissociation constants were determined using the nitrocellulose filter partitioning technique. Results are shown in Table 2. Binding of these ligands to VEGF in a buffer containing 10 mM dithiothreitol is at least 1000-fold weaker.

Receptor Binding

Unlabeled VEGF but not EGF was shown to inhibit binding of $^{125}$I-VEGF to HUVECs in a concentration-dependent manner (data not shown), confirming that $^{125}$I-VEGF binds to specific sites on HUVECs. As previous studies have reported (Myoken et al. (1991) Proc. Natl. Acad. Sci. USA 88:5819), two classes of receptors on HUVECs were observed to bind VEGF with dissociation constants of ~5×10$^{-11}$M (7,000 receptors/cell) and ~5×10$^{-10}$M (20,000 receptors/cell) (FIG. 6).

A group of truncated RNA ligands representing each of the sequence families (100t, family 1; 44t, family 2; 12t, family 3; 40t, family 4; 84t, family 5; and 126t, family 6 (SEQ ID NOS:51–56)), as well as random RNA were tested for their ability to inhibit binding of VEGF to its cell-surface receptors. All high-affinity ligands, but not random RNA, inhibited VEGF-VEGF receptor interaction in a concentration-dependent manner with half-inhibition occurring in the 20–40 nM range (FIG. 7).

EXAMPLE 4

MODIFIED 2'-NH$_2$ PYRIMIDINE RNA LIGANDS TO VEGF

In order to generate ligands with improved stability in vivo, two SELEX experiments (A and B) targeting VEGF were initiated with separate pools of randomized RNA containing amino (NH$_2$) functionalities at the 2'-position of each pyrimidine. Starting ligand pools for the two experiments contained approximately 10$^{14}$ molecules (500 pmols) of modified RNA randomized at 30 (SELEX experiment A) and 50 (SELEX experiment B) contiguous positions. The starting RNAs and the corresponding PCR primers are defined in FIG. 8 (SEQ ID NOS:57–62). Sequences corresponding to the evolved regions of modified RNA are shown in FIGS. 9A–G.

Ligands with similar primary structures were grouped into 5 families and their consensus sequences are shown below each sequence set FIGS. 9A–G (SEQ ID NOS:63–146). Groups of sequences with similar primary structure (families) have been aligned in FIGS. 9A–G and their consensus sequences are shown below each set. Pairs of similar/related sequences, sequences that could not be included in any of the families ("other sequences") and sequences that correspond to ligands that bind additionally to nitrocellulose filters with high affinity have been shown in separate groups. Letter N in a sequence indicates an ambiguous position on a sequencing gel. Italicized letter N in a consensus sequence indicates a position that is not conserved (i.e., any nucleotide may be found at that position). Dissociation constants for Random RNA A (30N8), Random RNA B (50N7) and a set of modified (2'- amino pyrimidine high-affinity RNA ligands for VEGF are shown in Table 3.

EXAMPLE 5

POST SELEX MODIFICATIONS OF VEGF RNA LIGANDS

In an attempt to further stabilize the nucleic acid ligands of the invention, certain post-SELEX modifications were done. The ligand NX107 (SEQ ID NO:147) was chosen as a model for post-SELEX modification. NX107 is a truncated version of Ligand 24A (SEQ ID NO:79) from Example 4. All of the pyrimidines in NX107 have an NH$_2$ group substituted at the 2'-position of the ribose. This example describes substitution of O-Methyl groups at the 2'-position of the ribose of certain of the purines of NX107. Additionally, phosphorothioate nucleotides were added at the 5' and 3' ends of the ligands and in at least one instance, at an internal position. The various substitutions to the ligand were designed to inhibit the activity of exonucleases and endonucleases, but not affect binding affinity.

To this end, certain ligands were synthesized and tested for binding affinity. The sequences and the results of the binding studies are provided in Table 4. The binding studies were performed using the protocols described in Example 1.

EXAMPLE 6

STABILITY OF POST-SELEX MODIFIED VEGF LIGANDS TO EX VIVO RAT TISSUE DEGRADATION

In order to be able to quickly assess the effects of ligand modifications on stability to tissue nucleases, the following assay was developed. Brain, kidney, liver and spleen tissues were removed from a freshly sacrificed rat, washed in saline to remove blood, and sliced into approximately 10 mm$^3$ pieces. Each piece was put into an Eppendorf tube with 50 µl PBS and quick frozen on dry ice. Tissues from the same rat were used for all the experiments described here. The ligand to be tested was 5'end-labeled with $^{32}$P, added to the thawed tissue slice in 80 µl PBS, and incubated at 37° C. Aliquots were withdrawn at 3, 10, 30, and 60 minutes, added to an equal volume of formamide dyes on ice, and quick-frozen on dry ice. The samples were run on a 20% denaturing acrylamide gel along with equal counts of the unincubated ligand, and a partial alkaline hydrolysate of the ligand (or a related ligand) for sequence markers. The gels were dried and exposed to X-ray film and a phosphorimager plate (for quantitation of degradation).

The VEGF ligands used in this study are shown in Table 4. Each ligand has the same core 24-mer sequence derived from a truncated 2'NH$_2$-pyrimidine SELEXed ligand (NX-107)(SEQ ID NO:147). NX-178 (SEQ ID NO:149) is the same 2'amino pyrimidine ligand with phosphorothioate backbone linked thymidine caps at the 5'- and 3'- ends of the ligand. NX-190 (SEQ ID NO:150) is an all DNA version of the same sequence with the above-described caps, and NX-191 (SEQ ID NO:151) is an all 2'OMe version. NX-213 (SEQ ID NO:152) is the capped amino ligand with all the purines 2'OMe substituted except four. NX-215 (SEQ ID NO:154) is the same as NX-213 with an internal phosphorothioate linkage between A7 and U8.

Tables 5 and 6 provide the results obtained by this assay on rat brain and kidney tissues as indicated by the percent of full length material found at the various time points. For this analysis, a ligand is still considered functionally intact with cuts in the phosphorothioate caps. The other tissues assayed had similar results. The post-SELEX modifications were successful in protecting the ligand from various endo- and exonucleases.

EXAMPLE 7

SSDNA LIGANDS TO VEGF

This example demonstrates the ability to obtain ssDNA ligands to vascular endothelial growth factor (VEGF).

Most of the materials and methods are the same as those described in Example 1. Two libraries of synthetic DNA oligonucleotides containing 40 random nucleotides flanked by invariant primer annealing sites were amplified by the Polymerase Chain Reaction (PCR) using oligonucleotide primers as shown in Table 7 (SEQ ID NOS:237–242). The protocols for the SELEX procedure are as described by Jellinek et al. (PNAS (1993) 90:11227–11231), in the SELEX Patent Applications and in Example 1. VEGF protein binding assays, receptor binding assays, and information boundary determinations are also described in Example 1.

The ssDNA ligands identified are shown in Table 8 (SEQ ID NOS:159–220). Only the sequence of the evolved region is provided in Table 8, however, each of the clones also includes the fixed regions of either SEQ ID NO:237 or SEQ ID NO:240. Clones named with numbers only include the fixed regions of SEQ ID NO:237 and clones named with b and number included the fixed regions of SEQ ID NO:240. Truncations (information boundary determinations) were performed on a number of ligands, which is also provided in Table 8 (SEQ ID NOS:221–230). Four sequence families were obtained from the alignment of the primary sequences of these ligands and a consensus sequence generated for each family (SEQ ID NOS:231–236). Orphan sequences were also identified. Select ligands were tested in the VEGF protein binding assay with results being shown in Table 8. The starting DNA random pool had a binding affinity Kd of approximately 200 nM. In the VEGF receptor binding assay, the truncated clone 33t (SEQ ID NO:224) had a Ki of 3 nM.

TABLE 1

Dissociation Constants For a Representative Set of Full-Length and Truncated High-Affinity RNA Ligands for VEGF.[a]

| LIGAND[b] | Kd1 (nM)[c] | X1[d] | Kd2 (nM)[e] | SEQ ID NOS. |
|---|---|---|---|---|
| 100 | 0.20 ± 0.02 | 0.82 ± 0.02 | 42 ± 30 | 11 |
| 100t | 0.42 ± 0.04 | 0.76 ± 0.03 | 182 ± 94 | 51 |
| 44 | 1.7 ± 0.5 | 0.70 ± 0.11 | 38 ± 32 | 20 |
| 44t | 0.48 ± 0.04 | 0.73 ± 0.01 | 82 ± 23 | 52 |
| 12 | 0.48 ± 0.07 | 0.56 ± 0.03 | 21 ± 5 | 22 |
| 12t | 1.1 ± 0.2 | 0.76 ± 0.04 | 180 ± 160 | 53 |
| 40 | 0.19 ± 0.09 | 0.19 ± 0.04 | 10 ± 1 | 28 |
| 40t[f] | 20 ± 1 | — | — | 54 |
| 84 | 0.82 ± 0.2 | 0.45 ± 0.06 | 21 ± 5 | 36 |
| 84t | 1.8 ± 0.4 | 0.53 ± 0.07 | 31 ± 10 | 55 |
| 126 | 0.14 ± 0.04 | 0.40 ± 0.04 | 11 ± 3 | 38 |
| 126t | 1.4 ± 0.2 | 0.54 ± 0.03 | 181 ± 57 | 56 |

[a]Binding experiments were done as described in Example 2 and errors are given as standard deviations.
[b]Full-length and truncated ligands are listed in pairs and represent sequence families 1–6, in order.
[c]Dissociation constant of the higher affinity binding component as defined in eq. 5.
[d]Mole fraction of the high-affinity binding component as defined in eq. 5.
[e]Dissociation constant of the lower-affinity binding component as defined in eq. 5.
[f]Dissociation constant for ligand 40t was determined by fitting the data points to eq. 2.

TABLE 2

Binding of 100t and 44t Truncates

| Target Molecule | 100t (Kd) (SEQ ID. NO. 51) | 44t (Kd) (SEQ ID. NO. 52) |
|---|---|---|
| bFGF | 1 μM | 0.6 μM |
| PDGF | 0.6 μM | 0.6 μM |
| antithrombin III | 3 μM | 12 μM |
| thrombin | >10 μM | >10 μM |
| plasminogen activator inhibitor I | >10 μM | >10 μM |

TABLE 3

| Ligand | Kd1, nM | X1 | Kd2, nM | SEQ ID NOS. |
|---|---|---|---|---|
| Rndm RNA A | 83 ± 21 | — | — | |
| Rndm RNA B | 240 ± 140 | — | — | |
| 14A | 0.70 ± 0.16 | 0.42 ± 0.05 | ~$10^2$ | 76 |
| 23A | 2.8 ± 0.3 | — | — | 78 |
| 24A | 0.71 ± 0.14 | 0.79 ± 0.5 | ~$10^2$ | 79 |
| 41A | 0.86 ± 0.19 | 0.68 ± 0.11 | ~$10^2$ | 93 |
| 17B | 0.028 ± 0.008 | 0.62 ± 005 | ~$10^2$ | 65 |
| 26B | 0.37 ± 0.10 | 0.74 ± 0.15 | ~$10^2$ | 82 |
| 30B | 0.034 ± 0.009 | 0.77 ± 0.06 | $10^1$–$10^2$ | 68 |
| 32B | 0.050 ± 0.023 | 0.50 ± 0.06 | 15 ± 9 | 104 |
| 34B | 0.068 ± 0.016 | 0.82 ± 0.06 | $10^1$–$10^2$ | 70 |
| 44B | 0.14 ± 0.06 | 0.54 ± 0.09 | 9 ± 6 | 95 |

TABLE 4

| SEQ ID NO: | Ligand | SEQUENCE | VEGF Protein Binding Kd | VEGF Receptor Binding Ki |
|---|---|---|---|---|
| 147 | NX-107 | ACC CUG AUG GUA GAC GCC GGG GU G | | 1 nM |
| 148 | NX-176 | ACC CU G AUG GUA GAC GCC GGG GUG | 65 nM | 10 nM |
| 149 | NX-178 T*T*T*T* | ACC CUG AUG GUA GAC GCC GGG GUG T*T*T*T*T | 0.7 nM | 1 nM |
| 150 | NX-190 T*T*T*T* | ACC CTG ATG GTA GAC GTT GGG GTG T*T*T*T*T | | |
| 151 | NX-191 T*T*T*T* | ACC CUG AUG GUA GAC GCC GGG GUG T*T*T*T*T | 120 nM | 500 nM |
| 152 | NX-213 T*T*T*T* | ACC CUG AUG GUA GAC GCC GGG GUG T*T*T*T*T | 0.2 nM | 1 nM |

TABLE 4-continued

| SEQ ID NO: | Ligand | SEQUENCE | VEGF Protein Binding Kd | VEGF Receptor Binding Ki |
|---|---|---|---|---|
| 153 | NX-214 T*T*T*T* | ACC CUG AUG GUA GAC GCC GGG GUG T*T*T*T*T | 0.2 nM | 1 nM |
| 154 | NX-215 T*T*T*T* | ACC CUG A*UG GUA GAC GCC GGG GUG T*T*T*T*T | 0.2 nM | 1 nM |
| 155 | NX-203 | ACC CUG AUG GUA GAC GCC GGG GUG | | |
| 156 | NX-204 | ACC CUG AUG GUA GAC GCC GGG GUG | | |
| 157 | NX-205 | ACC CUG AUG GUA GAC GCC GGG GUG | | |
| 158 | NX-206 | ACC CUG AUG GUA GAC GCC GGG GUG | | |

N = 2'OH
N = 2'NH$_2$
N = 2'OMe
N* = phosphorothioate
N = 2'deoxy
N = 2'OMe:2'OH::2:1

TABLE 5

EX VIVO RAT TISSUE STABILITY: BRAIN
PER CENT FULL LENGTH

| TIME (min.) | NX 107 | NX 178 | NX 190 | NX 191 | NX 213 |
|---|---|---|---|---|---|
| 3 | 94.82 | 100.48 | 99.61 | 98.09 | 100.33 |
| 10 | 91.66 | 96.27 | 99.23 | 97.75 | 99.81 |
| 30 | 79.47 | 86.98 | 97.53 | 96.54 | 99.00 |
| 60 | 73.04 | 79.39 | 96.37 | 95.45 | 99.02 |

TABLE 6

EX VIVO RAT TISSUE STABILITY: KIDNEY
PER CENT FULL LENGTH

| TIME (min.) | NX 107 | NX 178 | NX 190 | NX 191 | NX 213 |
|---|---|---|---|---|---|
| 3 | 90.34 | 96.07 | 99.05 | 97.07 | 100.01 |
| 10 | 69.97 | 96.55 | 97.13 | 97.76 | 100.13 |
| 30 | 46.30 | 92.37 | 94.56 | 98.53 | 99.40 |
| 60 | 45.00 | 90.14 | 91.83 | 97.75 | 99.09 |

TABLE 7

Starting Single Stranded DNAs and the Corresponding PCR
Primers Used in the ssDNA SELEX Experiments Targeting VEGF SELEX experiment A Starting ssDNA:
5'-ATCCGCCTGATTAGCGATACT(40N)ACTTGAGCAAAATCACCTGCAGGGG-3'
(SEQ ID NO: 237)
PCR Primer 1:
5'-JJJCCCCTGCAGGTGATTTTGCTCAAGT-3' (SEQ ID NO: 238)
PCR Primer 2:
5'-ATCCGCCTGATTAGCGATACT-3' (SEQ ID NO: 239)

SELEX Experiment B

Starting ssDNA:
5'-CTACCTACGATCTGACTAGC(40N)GCTTACTCTCATGTAGTTCCT-3'
(SEQ ID NO: 240)
PCR Primer 1:
5'-AJAJAGGAACTACATGAGAGTAAGC-3' (SEQ ID NO: 241)
PCR Primer 2:
5'-CTACCTACGATCTGACTAGC-3' (SEQ ID NO: 242)

J = biotin (from biotin phosphoramidite (e.g., Glen Research, Sterling, VA)

TABLE 8

VEGF ssDNA ligands
ssDNA bulk pool, BH SELEX: 0.44 nM

| SEQ ID NO: | ligand | | Kd, nM |
|---|---|---|---|
| | Family 1 | | |
| 159 | 3 | acaacggcgtggaagactagagtgcagccgaacgcatcta | |
| 160 | 5 | acgctacaagtccgctgtggtagacaagagtgcaggcaag | |
| 161 | 9 (3x) | aggcccgtcgaagntagagcgcagggccccaaaataccg | |
| 162 | 10 | gtaccatccacggtttacgtggacaagagggccctggtac | 1 |
| 163 | 11 | tcactacaagtccgccgtggtagacaagagtgcaggcaag | |
| 164 | 15 | accgctgtgtagttcctttaggactagagggccgcctac | 0.88 |
| 165 | 21 | taggcttgacgtcttctagactagagtgcagtcaaaccc | |
| 166 | 27 | tgcaggtcgactctagaggatccccgggtaccgagctcga | |
| 167 | 31 | acggtttacgtggacaagagggccctggtac | |
| 168 | 32 (3x) | ggtggactagaggncagcaaacgatccttggttcgcgtcc | 2 |
| 169 | 33 | tcaagcactcccgtcttccagacaagagtgcagggcctct | 2 |
| 170 | 35 | cgtgatggacaagagggccctatccaccggatatccgtc | |
| 171 | 37 | caagcagtgcccgtcttccagacaagagtgcaggcctct | |
| 172 | 39 | tgatccaccgtttatagtccgtggtagacaagagtgcagg | |
| 173 | 41 | aacacacaagaggacagttacaggtaacatccgctcagg | |
| 174 | 49 | agtggcgtctatagacaagagtgcagcccgagtttca | |
| 175 | 50 | ccacaagagggcagcaagtg-tacaactacagcgtccgg | |
| 176 | b56 (8x) | gcagggccacgtctatttagactagagtgcagtggttc | 0.5 |
| 177 | b69 | acggtccaaaggtttcccatccgtggactagagggcacgtgctta | |
| 178 | b80 | ccgtcgcgtgactataaccacacgcagactagagtgcagggctta | 8.1 |
| 179 | b81** | ccgaatggggctgcgactgcagtggacgtcacgtcgtta | 0.3 |
| 180 | b91** | acgcaagagagtcnccgaatgcagtctcagccgctaaca | |
| 231 | Consensus | agacaagagtgcagg | |
| 232 | | ggactagagggcagt | |
| SEQ ID NO: | ligand | | Kd PCR |
| | Family 2 | | |
| 181 | 2 | cannncactgcaagcaattgtggcccaaagggctgagt | |
| 182 | 14 | gctcgcttacaaaagggagccactgtagcccagactggac | |
| 183 | 25 (2x) | ggttatggtgtggttccgaatggtgggcaaagtaacgctt | |
| 184 | 40 | gcttgtngctccgaaggggcgcgtatccaaggacggttc | |
| 185 | 46 | tatggagtggttccgaatggtgggcaaagtaacgctt | |
| 186 | b54 | tgcnngcgggcggttctccggatgggaccataaggctttagctta | 2.5 |
| 187 | b55 | acaaggggtcctgnngaatggggggaatacgctagccgaa | 15 |
| 188 | b59 | aacacgagcatgtgggtcccttccgaatgggggtacaggctta | 91 |
| 189 | b79 | gaggcattaggtccgaatggtagtaatgctgtcgtgccttgctta | 2 |
| 190 | b81** | ccgaatggggctgcgactgcagtggacgtcacgtcgtta | 0.3 |
| 191 | b85 | gaggaggtgcgttgtccgaaggggtcgttagtcacctcgtgctta | 0.15 |
| 192 | b88 (5x) | gcaagggggtcctgccgaatggggggaatacgctagccgaaa | 34 |
| 193 | b89 (3x) | atccttccgaatgggggaaatggcgnccca | 2 |
| 194 | b91** | acgcaagagaggtcnccgaatggcagtctcagccgctaaca | 3.9 |
| 195 | b99 | cacgataatcctccgaaaagcgttgtccgaatgggtcgttagctta | 34 |
| 233 | Consensus | ctccgaatggggnaaa g | |
| | Family 3 | | |
| 196 | 18 | tatcaccccactggatagagccgcagcgtggccccctact | |
| 197 | 19 | gcccactgcatagagggacggttgtttccgcccggtgttt | |
| 198 | b51 | gtgaaggagccccaactggatagaagccttaaggcggtgt | |
| 199 | b60 | ccaccgcagagtgttacaccccataggagaagtccggatggctta | 26 |
| 200 | b62 | ccactgcatagagagtcgcaagacacggtgctttattcnccgctta | 2.9 |
| 201 | b63 | tgccccactggatagagtaggaggcctagccgacacggtgctta | |
| 202 | b65 | cgaggtcccccactggatagagttgttgaaacaacggttgcgctta | 0.53 |
| 203 | b66 | aacacttcccccactggatagaggcctttcgcagagccggtgctta | 1.3 |
| 204 | b95 | ccactgcatagagaactggatcgcacggtccaaagttcggtgctta | 0.9 |
| 205 | b96 | ccactgcatagagatactggattcgacnnnccaaagtttcggtgctta | 1.5 |
| 206 | b97 | ccactgcagagagtcaaccttacgangccaaggttgcggtgctta | >1 |
| 234 | Consensus | ccccactggatagag | |
| 235 | | ccccactgcatagag | |
| SEQ ID NO: | ligand | | Kd PCR |
| | Family 4 | | |
| 207 | 1 | tctgcgagagacctactggaacgttttgtgatattcaca | 12 |
| 208 | 6 | atacacccggcgggccctaccggatcgttgatttctctcc | 1.0 |
| 209 | 13 | acgcccctgagacctaccggaatnttntcgctaggccta | |
| 210 | 23 | gggcatctaacccagacctaccggaacgttatcgcttgtg | 0.75 |
| 211 | 44 | ggtgtgaaccagacctacnggaacgttatcgcttgtg | 0.4 |
| 236 | Consensus | agacctaccggaacgtt | |
| | Orphans | | |
| 212 | 4 | catcagtattatataacgggaaccaacggcaaatgctgac | |
| 213 | 7 | tccnngggagaatagggttagtcggagaagttaatcgct | |
| 214 | 16 | cgggaacgtgtggttacncggcctactggattgtttcctg | |
| 215 | 30 | ggtaggtccggtgtgaaagaggttcgcatcaggta | |
| 216 | 38 | cctcaggcaacatagttgagcatcgtatcgatcctggag | |
| 217 | 43 | ttggcttgagtcccggggacgcactgttgacagtggagt | |
| 218 | 45 | cagcaggttagtataacgggaaccaacggcaaatgctgac | |
| 219 | b53 | gcaagggcatctcggaatcggttaatctgacttgcaatacgctta | 2.5 |
| 220 | b98 | gatccacgaagaagcttactctcatgtagttcca | >100 |

TABLE 8-continued

VEGF ssDNA ligands
ssDNA bulk pool, BH SELEX: 0.44 nM

|     | Truncates |                                                |      |
| --- | --------- | ---------------------------------------------- | ---- |
| 221 | 10t       | gtaccatccacggtttacgtggacaagagggccctggtac       | 5    |
| 222 | 15t       | gtagttcctttaggactagagggccgcctac                | 3    |
| 223 | 32t       | tggactagaggncagcaaacgatccttggttcgcgtcc         | 17   |
| 224 | 33t       | cccgtcttccagacaagagtgcaggg                     | 0.7  |
| 225 | 56t       | agggccacgtctatttagactagagtgcagtggttc           | 0.2  |
| 226 | 85t       | ggaggtgcgttgtccgaaggggtcgttagtcacctc           | 0.3  |
| 227 | 88t       | gcaaggggtcctgccgaatgggggaatacgctagccgaaa       | 19   |
| 228 | 65t       | cgaggtcccccactggatagagttgttgaaacaacggtgcgctta  | 0.32 |
| 229 | 66t       | aacacttcccactggatagaggcctttcgcagagccggtgctta   | 0.35 |
| 230 | 23t       | gggcatctaacccagacctaccggaacgttatcgcttgtg       | >200 |

---

We claim:

1. A nucleic acid ligand to vascular endothelial growth factor (VEGF) identified according to the method comprising:
   a) contacting a candidate mixture of nucleic acids with VEGF, wherein nucleic acids having an increased affinity to VEGF relative to the candidate mixture may be partitioned from the remainder of the candidate mixture;
   b) partitioning the increased affinity nucleic acids from the remainder of the candidate mixture; and
   c) amplifying the increased affinity nucleic acids to yield a ligand-enriched mixture of nucleic acids, whereby a nucleic acid ligand to VEGF may be identified.

2. A purified and isolated non-naturally occurring nucleic acid ligand to VEGF.

3. The nucleic acid ligand of claim 2 which is a ribonucleic acid.

4. The RNA ligand of claim 3 wherein said ligand is selected from the group consisting of the sequences set forth in FIG. 2.

5. The RNA ligand of claim 3 wherein said ligand has been chemically modified at the ribose and/or phosphate and/or base positions.

6. The modified RNA ligand of claim 5 wherein said ligand is comprised of 2'-amino (2'-NH$_2$) modified nucleotides.

7. The modified RNA ligand of claim 6 wherein said ligand is selected from the group consisting of the sequences set forth in FIG. 9 and Table 4.

8. The nucleic acid ligand of claim 2 which is a deoxyribonucleic acid.

9. The DNA ligand of claim 8 wherein said ligand is selected from the group consisting of the sequences set forth in Table 8.

10. The nucleic acid ligand of claim 1 wherein the method further comprises modifying the nucleic acid ligand wherein said modifying comprises adding a moiety that decreases the activity of endonucleases or exonucleases on the nucleic acid ligand relative to the unmodified nucleic acid ligand, without adversely affecting the binding affinity of said nucleic acid ligand.

11. The nucleic acid ligand of claim 10 wherein said moiety comprises a phosphorothioate nucleotide.

12. The nucleic acid ligand of claim 1 wherein the method further comprises modifying the nucleic acid ligand wherein said modifying comprises substituting nucleotide residues, wherein said residues may be chemically modified, and wherein the modification decreases the activity of endonucleases or exonucleases relative to the unmodified nucleic acid ligand, without adversely affecting the binding affinity of said nucleic acid ligand.

13. The nucleic acid of claim 12 wherein said chemically modified residue comprises a 2'-O-Methyl (2'OMe) nucleotide.

14. A modified nucleic acid ligand of VEGF, wherein said ligand is modified to comprise the addition of a moiety to a nucleic acid ligand that decreases the activity of endonucleases or exonucleases on the nucleic acid ligand, without adversely affecting the binding affinity of said nucleic acid ligand.

15. The nucleic acid ligand of claim 14 wherein said moiety comprises a phosphorothioate nucleotide.

16. A modified nucleic acid ligand of VEGF, wherein the modification comprises the substitution of nucleotide residues of the nucleic acid ligand, wherein said residues may be chemically modified, and wherein said modification decreases the activity of endonucleases or exonucleases on the nucleic acid ligand relative to the unmodified nucleic acid ligand, without adversely affecting the binding affinity of said nucleic acid ligand.

17. The nucleic acid ligand of claim 16, wherein said chemically modified residue comprises a 2'-O-Methyl (2'-OMe) nucleotide.

18. The modified RNA ligand of claim 5 wherein said ligand is comprised of a 2'-O-Methyl (2'-OMe) modified nucleotide.

* * * * *

UNITED STATES PATENT AND TRADEMARK OFFICE
CERTIFICATE OF CORRECTION

PATENT NO. : 5,811,533
DATED : September 22, 1998
INVENTOR(S) : Larry Gold and Nebojsa Janjic It is certified that error appears in the above-identified patent and that said Letters Patent is hereby corrected as shown below:

At column 1, line 13, please delete "Methods of Producing".
At column 1, line 14, after "Ligands" please insert --to HIV-RT and HIV-1 Rev--.
At column 2, line 23, please delete "J. Biol. Chem. in press" and insert --J. Cell. Physiology $\underline{153}$:557--.
At column 2, line 24, please delete "$\underline{181}$:902-" and insert --$\underline{189}$:824--.
At column 2, line 51, please delete "Immunocompromized" and insert --Immunocompromised--.
At column 3, lines 10-11, please delete "Table 9" and insert --Figure 9--.
At column 4, line 51, before "U.S." please insert --now United States Patent No. 5,475,096,--.
At column 4, line 53, after "entitled" please insert --Methods for Identifying--.
At column 5, line 64, before "methods" please insert --now United States Patent No. 5,496,938,--.
At column 5, line 66, please delete "Methods of Producing".
At column 5, line 67, after "Ligands" please insert --to HIV-RT and HIV-1 Rev--.
At column 8, line 7, please delete "bFGF" and insert --VEGF--.
At column 8, line 18, please delete "(OAc)2" and insert --$(OAc)_2$--.
At column 8, line 38, please delete "than" and insert --then--.
At column 9, line 39, please delete "$\alpha\text{-}^{32}pCp$" and insert --$\alpha\text{-}^{32}PCp$--.
At column 10, line 16, before "SEQ" please insert --Figure 1;--.

UNITED STATES PATENT AND TRADEMARK OFFICE
CERTIFICATE OF CORRECTION

PATENT NO. : 5,811,533
DATED : September 22, 1998
INVENTOR(S) : Larry Gold and Nebojsa Janjic It is certified that error appears in the above-identified patent and that said Letters Patent is hereby corrected as shown below:

At column 10, line 45, please delete "(1988)" and insert --(1989)--.
At column 10, line 55, please delete "(1988)" and insert --(1989)--.
At column 11, line 8, please delete "Figs. 3A-F" and insert --Fig. 3A--.
At column 11, line 32, please delete "Figs. 3A-F" and insert --Fig. E--.
At column 12, line 32, please delete "Figure 4" and insert --Figures 4A-F--.

Signed and Sealed this

Thirtieth Day of March, 1999

Attest:

Q. TODD DICKINSON

*Attesting Officer*   *Acting Commissioner of Patents and Trademarks*